US012025553B2

United States Patent
Lhoest et al.

(10) Patent No.: US 12,025,553 B2
(45) Date of Patent: Jul. 2, 2024

(54) DEVICE AND METHOD FOR THE CONTACTLESS DETERMINATION OF AT LEAST ONE PROPERTY OF A METAL PRODUCT

(71) Applicants: SMS group GmbH, Düsseldorf (DE); Drever International S.A., Angleur (BE)

(72) Inventors: Alexandre Lhoest, Eupen (BE); Oliver Pensis, Montegnee (BE); Ulrich Sommers, Düsseldorf (DE); Vincent Housen, Juprelle (BE)

(73) Assignees: SMS group GmbH, Düsseldorf (DE); Drever International S.A., Angleur (BE)

( * ) Notice: Subject to any disclaimer, the term of this patent is extended or adjusted under 35 U.S.C. 154(b) by 398 days.

(21) Appl. No.: 17/617,958

(22) PCT Filed: Jun. 15, 2020

(86) PCT No.: PCT/EP2020/066494
§ 371 (c)(1),
(2) Date: Jan. 17, 2022

(87) PCT Pub. No.: WO2020/249820
PCT Pub. Date: Dec. 17, 2020

(65) Prior Publication Data
US 2022/0260482 A1   Aug. 18, 2022

(30) Foreign Application Priority Data

Jun. 14, 2019  (DE) .................. 10 2019 208 705.1

(51) Int. Cl.
 G01N 21/17 (2006.01)
 C21D 11/00 (2006.01)
 (Continued)

(52) U.S. Cl.
CPC ....... G01N 21/1702 (2013.01); C21D 11/005 (2013.01); G01N 23/083 (2013.01);
(Continued)

(58) Field of Classification Search
CPC .... G01N 21/00; G01N 21/17; G01N 21/1702; G01N 23/00; G01N 23/08; G01N 23/083;
(Continued)

(56) References Cited

U.S. PATENT DOCUMENTS 2,914,676 A    11/1959  Hendrik et al.
5,654,977 A    8/1997   Morris
(Continued)

FOREIGN PATENT DOCUMENTS

DE   102008008829 A1   8/2008
DE   102017208576 A1   11/2017
(Continued)

OTHER PUBLICATIONS

Wehrhahn D, "Berührungslose Lasermessung in der Aluminium- und Stahlindustrie", Apr. 15, 2019, retrieved from https://www.drwehrhahn.de/fileadmin/redakteure/dokumente/de/anwendungsbereiche/stahl_de.pdf on Nov. 11, 2021.

Primary Examiner — Nguyen Q. Ha
(74) Attorney, Agent, or Firm — Smartpat PLC

(57) ABSTRACT

A device for the contactless determination of at least one property of a metal product during the metallurgical production of the metal product comprises a housing and at least one measuring device comprising a transmitting unit and a receiving unit. An electromagnetic field is generated by the transmitting unit and directed onto the metal product, thereby inducing a physical interaction in the material of the metal product, and a remaining and/or resulting part of this physical interaction is subsequently received by the receiving unit. At least one component of the measuring device (Continued)

comprising the transmitting unit and/or the receiving unit can be moved relative to the housing or the metal product moving therein, in order to thereby set or selectively change a predetermined distance to the metal product for the transmitting unit and/or the receiving unit.

38 Claims, 14 Drawing Sheets

(51) Int. Cl.
    *G01N 23/083*     (2018.01)
    *G01N 27/72*     (2006.01)
    *G01N 33/204*     (2019.01)

(52) U.S. Cl.
    CPC ........... *G01N 27/72* (2013.01); *G01N 33/204* (2019.01); *G01N 2021/1706* (2013.01); *G01N 2201/06113* (2013.01); *G01N 2223/04* (2013.01); *G01N 2223/624* (2013.01)

(58) Field of Classification Search
    CPC ........ G01N 27/00; G01N 27/72; G01N 33/00; G01N 33/20; G01N 33/204; G01N 2021/06113; G01N 2021/1706; G01N 2223/04; G01N 2223/624; C21D 11/00; C21D 11/005

See application file for complete search history.

(56) References Cited

U.S. PATENT DOCUMENTS

| | | |
|---|---|---|
| 6,068,539 A | 5/2000 | Bajaj et al. |
| 6,254,459 B1 | 7/2001 | Bajaj et al. |
| 2003/0038630 A1 | 2/2003 | Daalmans et al. |
| 2019/0292624 A1* | 9/2019 | Biglari ................. G01N 33/204 |
| 2021/0148859 A1 | 5/2021 | Hino et al. |
| 2021/0164957 A1 | 6/2021 | Monfort et al. |

FOREIGN PATENT DOCUMENTS

| | | |
|---|---|---|
| EP | 0941806 B1 | 1/2003 |
| FR | 1106945 A | 12/1955 |
| JP | S5164340 A | 12/1980 |
| JP | S5662917 A | 5/1981 |
| JP | H10239256 A | 9/1998 |
| WO | 0146682 A2 | 6/2001 |
| WO | 2016185012 A1 | 11/2016 |
| WO | 2017202904 A1 | 11/2017 |
| WO | 2019003727 A1 | 1/2019 |
| WO | 2019228692 A1 | 12/2019 |

* cited by examiner

DEVICE AND METHOD FOR THE CONTACTLESS DETERMINATION OF AT LEAST ONE PROPERTY OF A METAL PRODUCT

TECHNICAL FIELD

The disclosure relates to a device for the contactless determination of at least one property of a metal product during the metallurgical production of the metal product, and to a corresponding method.

BACKGROUND

According to the prior art, it is known in the manufacture of metallic products that, for example, properties of the metal products are also determined or checked, as the case may be, for the purpose of quality assurance. For this purpose, measuring devices that ensure the contactless and non-destructive determination of properties of the metal product are used. In connection with furnace devices or the like, where high temperature is usually present, such measuring devices are, as a rule, located outside the housing of the furnace. The problem in this case is that the components of the measuring device cannot easily be arranged in the direct vicinity of the metal product. Furthermore, complex cooling for the components of the measuring device with appropriate temperature management is required such that the components are not damaged by the high temperature of a furnace or the metal product.

From WO 2019/228692 A1, determining the austenite content of a metal product by using electromagnetic radiation in real time is known. For this purpose, two coils fed with AC voltage are used, between which the metal product is moved. One of the two coils emits electromagnetic radiation toward the metal product, wherein the resulting wave pattern of electromagnetic radiation that has passed through the metal product is received by the other coil. The distance between the two coils is set to a certain value, wherein a change to such distance—once set—is not foreseen.

According to the prior art, the contactless and non-destructive determination of the properties of a metal product during its metallurgical production can also be carried out according to the principle of X-ray diffraction. This is known, for example, from WO 2017/202904 A1, with which the microstructure of a metal product is determined by using an X-ray source and an X-ray detector, wherein the X-ray source and the X-ray detector are each arranged in an actively cooled receiving chamber. The metal product to be inspected is moved past between the X-ray source and the X-ray detector, wherein a disadvantage is that the distance between the X-ray source and the X-ray detector relative to each other or the distance between these two measuring components and the metal product is invariable. In the case of the technology in accordance with WO 2017/202904 A1, the disadvantageous problem is that the distance between, on the one hand, the X-ray source and the X-ray detector and, on the other hand, the metal product is comparatively large and cannot be brought to smaller values in terms of plant technology.

The determination of material properties of a metal product using the principle of X-ray diffraction is also known from JP 56062917 A. In this case, a furnace device through which a metal product is passed for tempering or "quenching," as the case may be, is equipped with a measuring device, by means of which X-ray radiation are directed onto the metal product, in order to precisely determine the austenite content of the metal product. Such measuring device is fixedly arranged outside the housing of the furnace device and thereby in a constriction or narrow point, as the case may be, of the housing, such that the distance of the measuring device to the metal product is thereby reduced. Due to the geometry of the specified narrow point of the housing of the furnace device, the distance of the measuring device to the metal product is fixed and cannot be changed.

SUMMARY

The disclosure is based on the object of creating a technology for the contactless and interference-free determination of the material properties of a metal product, with which the determination of at least one property of the metal product is optimized and possible with greater variability compared to the prior art discussed above.

This object is achieved by a device as described herein and by a method as described herein.

A device for the contactless determination of at least one property of a metal product during the metallurgical production of the metal product comprises a housing through which the metal product can be moved. It further comprises at least one measuring device comprising a transmitting unit and a receiving unit. An electromagnetic field is generated at least by the transmitting unit and directed onto the metal product, thereby inducing a physical interaction in the material of the metal product. A remaining and/or resulting part of this physical interaction can be received by the receiving unit. A first opening and a second opening are formed in the wall of the housing. Thereby, the transmitting unit of the measuring device is associated with the first opening, such that the electromagnetic field generated by the transmitting unit and/or its associated field lines impinges on the metal product on the side of the first opening. Furthermore, the receiving unit of the measuring device is associated with the second opening, such that the remaining and/or resulting part of the physical interaction induced in the material of the metal product can be received or detected, as the case may be, by the receiving unit on the side of the second opening. The device comprises at least one adjusting device, in particular provided outside the housing, by means of which at least one component of the measuring device comprising the transmitting unit and/or the receiving unit can be moved in the region of an opening of the housing or adjacent thereto and relative to the wall of the housing or relative to the metal product guided inside the housing, as the case may be, in order to thereby set or selectively change a predetermined distance for such component, i.e. for the transmitting unit and/or the receiving unit, from the metal product moved inside the housing.

Similarly, the disclosure also provides a method for the contactless determination of at least one property of a metal product during the metallurgical production of the metal product. With this method, the metal product is moved through a housing of a device. In any case, the method uses at least one measuring device comprising a transmitting unit and a receiving unit, wherein an electromagnetic field is generated at least by the transmitting unit and is directed onto the metal product, by which a physical interaction is induced or caused, as the case may be, in the material of the metal product. Subsequently, the remaining and/or resulting part of this physical interaction is received by the receiving unit. The method is characterized in that at least one component of the measuring device comprising the transmitting unit and/or the receiving unit is moved relative to the housing or the metal product moved therein, as the case may be, and in the region of an opening of the housing or adjacent thereto, in order to thereby set or selectively change a predetermined distance to the metal product for this component.

With regard to the feature "metallurgical production of a metal product," it should be pointed out at this point that, in the sense of the present disclosure, this also includes a heat treatment of the metal product, which is carried out in or with a furnace device and is intended, for example, to temper or anneal, as the case may be, the metal product. Accordingly, the housing through which the metal product is moved or guided, as the case may be, can be part of a furnace for heat treatment.

Additionally, or alternatively, it can also be provided that the housing through which the metal product is moved or guided, as the case may be, is part of a system for coating the metal product.

Furthermore, it may be pointed out separately at this point that the metal product, the properties of which can be determined with the device, is not as such part of this device. Rather, the housing of the device is suitable or designed for the metal product to be moved or guided through the housing in one direction of movement during its metallurgical production.

With regard to the heat treatment specified above of the metallic product, it is thus to be understood for the device and the corresponding method that the contactless determination of at least one property of the metallic product can in particular also be carried out if the metallic product is either exposed to comparatively high temperatures, for example in a furnace for heat treatment, and/or itself still has a comparatively high temperature.

The disclosure is based on the essential finding that it is possible to move or adjust, as the case may be, at least one component of the measuring device, i.e., the transmitting unit or the receiving unit, or both of these components of the measuring device, i.e. the transmitting unit and the receiving unit, relative to the wall of the housing through which the metal product is passed. Through such a movement, the distance of the transmitting unit and the receiving unit relative to each other, and/or thus at the same time also the distance of the transmitting unit and/or the receiving unit to the metal product guided within the housing, can be set or selectively changed, for example also "online" or during an ongoing measurement of the material properties of the metal product and/or during its metallurgical production.

With regard to a predetermined distance between, on the one hand, the components of the measuring device, i.e., the transmitting unit and/or the receiving unit, and, on the other hand, the metal product, it may be pointed out at this point that this distance can be 100 mm, for example. By the present disclosure, it can be achieved that this distance is as small as possible and can assume a value that is preferably smaller than 50 mm, further preferably smaller than 30 mm, further preferably smaller than 20 mm and further preferably can be about 10 mm. In this context, it is also noted that the predetermined distance is also adapted to the design or dimensions, as the case may be, of the transmitting unit and/or receiving unit. For example, the distance of the receiving unit from the metal product also depends on the dimensions or size, as the case may be, of the receiving unit. This also applies in the same manner to the transmitting unit. In any case, the predetermined distance between, on the one hand, the transmitting unit and/or receiving unit and, on the other hand, the metal product is set in such a manner that the respective specifications with regard to product stability are thereby also taken into account.

In an advantageous further development, the adjusting devices for moving the components of the measuring device can each have a high response speed and a high adjustment speed. Taking this into account, a predetermined distance between, on the one hand, the transmitting unit and/or the receiving unit and, on the other hand, the metal product can also be set to values of less than 10 mm. Details of this are described separately below.

In an advantageous further development, the housing has a narrow point in the region of the first opening and/or the second opening. By moving a component of the measuring device, i.e. the transmitting unit and/or the receiving unit, in the region of or within these openings of the housing or adjacent thereto in the direction of the metal product, which then applies in the same manner to the narrow point, a resulting distance between, on the one hand, the transmitting unit and/or the receiving unit and, on the other hand, the metal product can be further reduced thanks to the specified narrow point.

With regard to the "predetermined distance" feature between a component of the measuring device (=transmitting unit and/or receiving unit) and the metal product, it may be pointed out separately at this point that this distance is selected in the sense of the present disclosure in each case in adaptation to the physical principle with which, for example, waves are generated by the transmitting unit and directed onto the metal product. Stated differently, this predetermined distance between, on the one hand, the transmitter/receiver unit and, on the other hand, the metal product is adapted in each case to the type of electromagnetic field generated by the transmitting unit (e.g., X-ray radiation or laser radiation) or to the magnetic field generated by the transmitting unit and acting on the metal product. As a rule, this predetermined distance is selected to be as small as possible and can assume one of the exemplary values specified above.

The movement of the transmitting unit and/or the receiving unit relative to the wall of the housing is preferably carried out translationally, for example using at least one adjusting device, which is arranged in particular outside the housing through which the metal product is moved or guided, as the case may be, and is suitably operatively connected to the transmitting unit or receiving unit, as the case may be. Such an adjusting device can be of telescopic design, by which a large adjustment range for moving into or out of the housing is achieved by simple means for the transmitting unit or receiving unit, as the case may be, connected thereto. Such a telescopic adjusting device also has the advantage that it requires only a small amount of installation space.

A further advantage with respect to the mobility specified above of the components of the measuring device is that it is thus possible to bring the transmitting unit and/or the receiving unit, preferably both of these units together, out of the housing of the device and subsequently to space them and/or remove them from the housing. This then simplifies possible calibration work and/or maintenance work for these components of the measuring device.

The principle of the contactless determination of at least one property of the metal product during its metallurgical production is based on the fact that an electromagnetic field is generated by the transmitting unit, which is directed onto the metal product. In other words, the metal product is arranged or moved, as the case may be, with respect to the transmitting unit in such a manner that the metal product is in the area of influence of the field lines of the electromagnetic field generated by the transmitting unit. On the basis of this, the mentioned physical interaction is then caused or induced, as the case may be, in the material of the metal product.

In accordance with the present disclosure, the physical interaction specified above can be based on the following technical aspects:

- Transmission of an electromagnetic radiation, in particular X-ray radiation, through the material of the metal product ("transmission or passage principle"), wherein the part of the radiation (preferably X-ray radiation) that passes through the metal product is influenced by the properties of the metal product;
- Reflection of an electromagnetic radiation, in particular laser radiation, at the material of the metal product and/or at its surface ("reflection principle"), wherein the reflected part of the radiation (preferably laser radiation) is influenced by the properties of the metal product;
- Magnetization of the metal product, which accordingly consists of a magnetizable metal such as in particular steel, by the electromagnetic field generated by the transmitting unit, the residual magnetic field strength and/or its gradient, which can be detected by the receiver unit(s), being influenced by the properties of the metal product;
- Introducing electromagnetic radiation, in particular in the form of laser radiation emitted by the electromagnetic field generated by the transmitting unit, into the material of the metal product, as a result of which a local ultrasonic field is generated in the material of the metal product, which field can be measured or detected, as the case may be, by the receiving unit, for example also on the basis of laser radiation directed onto the metal product.

In principle, with regard to the radiation emanating from the electromagnetic field generated by the transmitting unit, it is noted that this can be any form of electromagnetic radiation with which it is possible to determine at least one property of the metal product, for example—as already mentioned above—X-ray radiation or laser radiation, or alternatively microwaves, infrared or with wavelengths in the visible range.

With respect to the electromagnetic radiation that may be generated by the transmitting unit as described above, in the event that the transmitting unit and receiver unit are arranged on respective opposite sides of the metal product, it is understood that the waves generated by the transmitting unit, preferably of X-ray radiation, pass through the metal product, wherein the remaining and/or resulting wave pattern are then received by the receiving unit on the opposite side of the metal product.

In the event that the transmitting unit and the receiving unit are each arranged on the same side of the metal product, the radiation, preferably laser radiation, generated by the transmitting unit is reflected on a surface of the metal product, and subsequently the remaining and/or resulting wave pattern, for example of the laser radiation, is received by the receiving unit. For this case, it can also be provided that the first and second openings of the housing are combined into a common opening. This means that a common and sufficiently large opening is then formed for these components of the measuring device on the side of the housing on which the transmitting unit and the receiving unit are arranged.

In an advantageous further development, the transmitting unit and receiver unit can be part of an IMPOC measuring head. The IMPOC measuring principle (IMPOC="impulse magnetic process online controller") is based on the fact that, for example, a steel strip is shock-magnetized at regular intervals with the aid of current-carrying coils and the residual magnetic field strength of the locally generated magnetization or a gradient calculated from this, as the case may be, is measured by means of a receiver unit in the form of a magnetic field sensor. Specifically, the measured value of the residual magnetic field strength or the calculated gradient is assigned the mechanical strength of the section of the metal product under investigation via correlation relationships, wherein this mechanical strength comprises in particular the tensile strength and the yield strength of the material of the respective metal product. In other words, the resulting or remaining, as the case may be, magnetic properties of the metal product are measured by the receiver unit (remanence or hysteresis curve).

With the IMPOC method, the residual field strength is measured in the unit $[A/m^2]$.

The IMPOC measuring principle is limited to magnetizable steel grades, wherein associated measuring equipment is commercially available.

With regard to an IMPOC measuring head, it may be additionally pointed out that here the transmitting unit is in the form of a magnetizing coil, and the receiving unit is in the form of a magnetic field sensor. If such an IMPOC measuring head is arranged on one side of the metal product, it is understood in view of the fact that, as described, the magnetizing coil and the magnetic field sensor are integrated in this measuring head, then—generally speaking—the transmitting unit and the receiving unit are arranged on the same side of the metal product. In addition, it should be noted that the IMPOC measuring method generally involves the use of two measuring heads, which are preferably of identical design and are arranged on opposite sides of the metal product to be examined. For the purposes of the present invention, these two measuring heads can each be understood as a measuring device.

In accordance with an advantageous further development, with regard to an embodiment of the housing having openings with which the transmitting unit and receiving unit are associated, the movement of the transmitting unit and/or the receiving unit by means of the associated adjusting device can be effected in such a manner that the transmitting unit and/or the receiving unit are moved into the housing through the openings associated with them respectively or are moved out of the housing to the outside. Thereby, as already described above, the distance between, on the one hand, the transmitting unit and/or the receiving unit and, on the other hand, the metal product is set to a predetermined value or selectively changed. If the transmitting unit and/or the receiver unit of the measuring device are moved into the housing by means of the associated adjusting device, an advantageously very small distance of these component(s) of the measuring device from the metal product can thereby be achieved.

In accordance with an advantageous further development, an adjusting device, to which the transmitting unit and/or the receiving unit is operatively connected in each case and, as described, a movement of these components of the measuring device relative to the housing of the device is realized, is arranged outside the housing. A large adjustment travel for such an adjusting device can be achieved in a robust manner by a telescopic design of this adjusting device. Alternatively, it is also possible to provide at least one adjusting device for moving the transmitting unit and/or the receiver unit within the housing.

If the housing is a furnace for heat treatment of the metal product, such housing usually contains a certain gas atmosphere of high temperature, which must be sealed with respect to the surrounding area of the housing. For this purpose, in accordance with an advantageous further development, shields are provided, which both ensure the sealing of the interior space of the housing from the external surrounding area and, at the same time, are transparent with respect to the waves of electromagnetic radiation generated by the transmitting unit. For example, such shields may be windows. In any case, it is pointed out in this connection that the shields or windows, as the case may be, have the required permeability specified above with respect to the radiation waves of an electromagnetic field and/or with respect to the remaining and/or resulting part of the physical interaction described above. This makes it possible to arrange both the transmitting unit and the receiving unit each on an outer side of these shields or windows, as the case may be, which is opposite to the interior space of the housing.

With regard to the possibility that the housing of the device can be part of a furnace for heat treatment, it is also pointed out at this point that there is a potential hazard from the gases that may be contained in such a furnace, for example hydrogen, nitrogen or combustion gases. Accordingly, effective sealing of the first and second openings formed in the wall of the housing from the surrounding area is important in this regard.

In an advantageous further development, the specified shields, with which a sealing of the interior space of the housing from the external surrounding area is achieved in the region of the openings of the housing, are designed in such a manner that a reduction of the heat radiation is also achieved with such shields. This means that a comparatively high temperature inside the housing is suitably reduced by such shields or windows with the consequence that a reduced temperature prevails on the opposite side of such shields or windows on which a component of the measuring device, i.e., a transmitting unit or receiving unit is arranged.

As described above, shields, in particular in the form of windows, are provided in the region of each of the first and second openings of the housing, by means of which, in addition to sealing off the atmosphere or gas composition prevailing inside the housing from the surrounding area, a reduction in thermal heat radiation is also achieved. According to an advantageous further development, in order to achieve even better mobility of the transmitting unit and/or the receiving unit with respect to the smallest possible distance from the metal product, a shield is connected to a sealing device, in particular an elastically deformable sealing device, wherein the sealing device is fastened to the edges of the first or second opening, and the interior space of the housing is thereby sealed off from the surrounding area.

The sealing device just mentioned is connected to suitable adjusting means. Thereby, it is possible to move the sealing device together with the associated shield (e.g., in the form of a window) into or out of the housing. It is expedient that such adjusting means is of telescopic design, by which a large adjustment travel can be achieved in a simple and, in particular, space-saving manner.

If a sealing device attached to the edges of the first opening and the second opening has been moved into the housing, for example, the associated transmitting unit/receiving unit can also be moved into the housing in adaptation thereto or to the same extent, as the case may be, in order to thereby achieve the smallest possible distance from the metal product, or to set or selectively change a predetermined distance from the metal product.

The sealing device described above, which is particularly flexible, can be in the form of a deformable bellows.

A shaping can be provided for the sealing device specified above, in particular a flexible one, such that it is formed to be round, rounded, oval, rectangular or square in cross-section or has a combination of such shapes.

In an advantageous further development, it can be provided that the sealing device, in particular the flexible sealing device, is equipped with a protective layer and/or insulation against electromagnetic and/or thermal radiation on its front side facing the interior space of the housing and/or lateral sections of the sealing device. Thereby, the advantage is achieved that such a sealing device is less sensitive and has a longer service life if it is attached to the edges of the first or second opening of the housing, as described, and is thus arranged in the immediate vicinity of the interior space of the housing, in which very high temperatures may prevail. Mutatis mutandis, this also applies with respect to the electromagnetic radiation to which the sealing device can be exposed.

The essential components of the measuring device, specifically the transmitting unit and receiver unit, are sensitive components that must be protected in particular against the effects of excessive temperatures. For this reason, such components without protection are not placed directly inside the housing, in which very high temperatures usually prevail, or placed inside it—instead, the transmitting unit and the receiving unit are always separated from the interior space of the housing by the shields, e.g., in the form of windows, through which there is also a reduction in heat radiation, as described above.

For further protection against high temperatures, in accordance with an advantageous further development, at least one cooling device can be provided. Such cooling device serves the purpose of cooling the shields or windows, as the case may be, provided in the region of the first or second opening, as the case may be, of the housing and/or the components of the measuring device (transmitting unit and/or receiving unit) and/or the sealing device. For this purpose, it can be provided that the cooling devices comprise cooling lines and/or cavities, which are formed in a wall of the housing, in particular in a manner adjacent to the first window and/or second window, and through which a cooling fluid flows, in particular in the form of a liquid. Additionally, or alternatively, it can be provided that cooling lines and/or cavities of the cooling device are provided in the material of the sealing device, and/or that cooling lines, in particular in the form of line coils, are provided on at least one component of the measuring device (transmitting unit and/or receiving unit).

During practical use of the present invention, it is further significant that the shields, preferably in the form of windows, remain free of any form of dust, dirt or the like. For this purpose, according to an advantageous further development, at least one purge gas device is provided, by means of which a purge gas is applied to the shields or windows, as the case may be. Purge gas can be discharged through suitable nozzles of the purge gas device, which are arranged on the outer side of the shields or windows, of the case may be, and/or on their inside, i.e., in the interior space of the housing. Thus, the surface of the shields or windows, as the case may be, is preferably permanently "blown free" by the discharge of the purge gas during the use of the device or during the implementation of the method in accordance with the present invention. As a result, the surface of such shields or windows, as the case may be, remains essentially free of debris in the form of dust or other contaminants.

In addition, it should be noted at this point that the discharge of purge gas to the outer side of the shields or windows can also contribute to cooling such shields or windows.

With respect to the at least one property of the metal product that can be determined by means of the present disclosure, it may be noted in this place that the property of the metal product may be the following quantities:

Microstructure,
Phase fraction,
Degree of recrystallization,
Grain size,
Texture,
Pole figure,
Orientation distribution function,
Oxidation layer, and/or
Mechanical characteristic value of the metal product.

In an advantageous further development, several measuring devices, each with a transmitting unit and a receiving unit, can also be used. For this case, correspondingly large openings or a plurality of openings can then also be formed in the wall of the housing, to which the individual transmitting units/receiving units of the respective measuring device are assigned.

In an advantageous further development, the openings that are formed in the wall of the housing and with which the respective components of the measuring device are associated may be provided with a high-performance insulating material. The same applies to the narrow point that may be formed in the wall of the housing in the region of the first and/or second opening. In any case, such an insulating material achieves the advantage that less thermal radiation acts on a sealing device, which can be fastened to the edges of a respective opening, and/or on a component of the measuring device (transmitting unit and/or receiving unit), which can be moved relative to the wall of the housing in the region of such an opening or adjacent thereto, as described above.

The use of the present disclosure is particularly suitable in the heat treatment of a metal product, i.e., in conjunction with a furnace device through which the metal product is passed in the course of its heat treatment. In this case, it is then possible with the aid of the present disclosure to determine "online" or in real time at least one property of the metal product. In the course of this, it is also possible, on the basis of the measured value for the at least one property of the metal product, to influence its manufacturing process, preferably with a controlled system.

Preferred embodiments are described in detail below with reference to a schematically simplified drawing.

DETAILED DESCRIPTION

Figure 1:
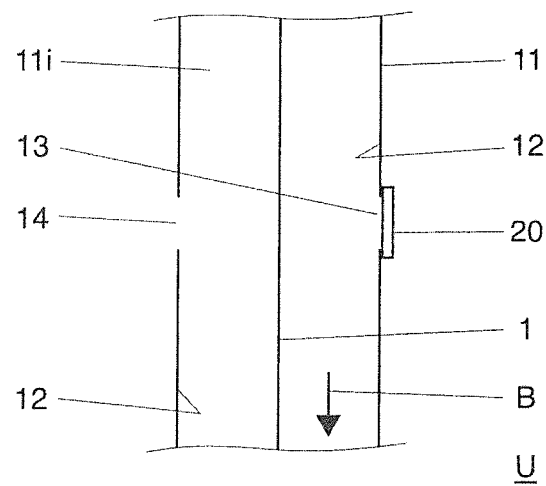
FIGS. 1-4 show possible embodiments for a housing of a device as described.

With reference to FIGS. 1-25, preferred embodiments of a device 10 and a corresponding method are shown and described below in order to determine at least one property of a metal product 1 during its metallurgical production. Identical features in the drawing are each provided with the same reference signs. At this point, it is separately pointed out that the drawing is only simplified and in particular shown without scale.

The device 10 comprises a housing 11 with an interior space 11i. A metal product 1, for example in the form of a cold or hot strip, can be passed through the interior space 11i of the housing 11. The direction of movement in which the metal product 1 is passed through the housing 11 is designated in each case by "B" in the drawing and indicated by an arrow or a corresponding symbol.

At least a first opening 13 and a second opening 14 are formed in a wall 12 of the housing 11 of the device 10. If such two openings 13, 14 are formed on the same side of the housing 11, such openings 13, 14 can also be combined into a common opening G, if necessary, which is described separately below (see FIG. 23, FIG. 24).

In the region of the openings 13, 14 of the housing 11 of the device 10, shields 20 are arranged in each case, which are formed, for example, in the form of windows. Without seeing any limitation in this, such shields will always be referred to hereinafter only as "windows" 20. Such windows 20 are part of a sealing concept in accordance with the present invention, in order to thereby achieve a sealing of the interior space 11i of the housing 11 with respect to the surrounding area U.

The embodiment of FIG. 1 shows a longitudinal sectional view through the housing 11 of a device. As can be seen, a metal product 1 is moved through the housing 11 along a direction of movement B (from top to bottom in the drawing plane of FIG. 1). The surrounding area of the housing 11 or its outer side, as the case may be, is symbolically designated by "U." The first window 13 and the second window 14 are formed in the wall 12 of the housing on opposite sides of the metal product 1. In this case, the windows 20 are fastened directly to the edges of the respective openings 13, 14 or within such openings, as the case may be, wherein, for the sake of simplification and for better illustration, the window 20 for the second opening 14 is not shown in FIG. 1.

Figure 2:
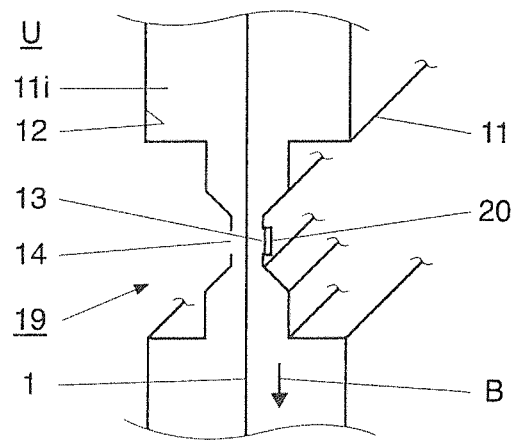
Figure 3:
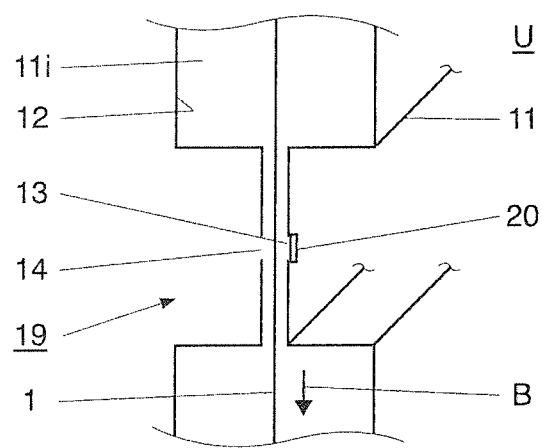
Figure 4:
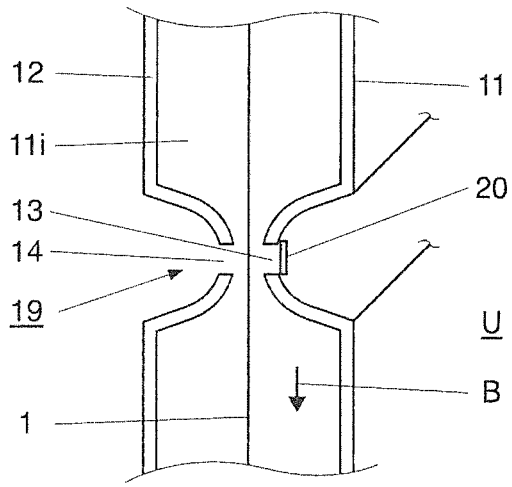

The embodiments in accordance with FIGS. 2-4 differ from the embodiment of FIG. 1 in that the housing 11 has a narrow point 19 in the region of the first and second openings 13, 14. Otherwise, the embodiments in accordance with FIGS. 2-4 differ only in the geometry of the narrow point 19, such that, to avoid repetition, reference is made to the description of FIG. 1.

The device 10 comprises at least one measuring device 16 (see FIG. 5), which consists of a transmitting unit 17 and a receiving unit 18.

The components of the measuring device 16, i.e., the transmitting unit 17 and the receiving unit 18, are each operatively connected to an adjusting device 15a. When the respective adjusting device 15a is actuated, the transmitting unit 17 or receiver unit 18, as the case may be, can be moved relative to the wall 12 of the housing.

Figure 5:
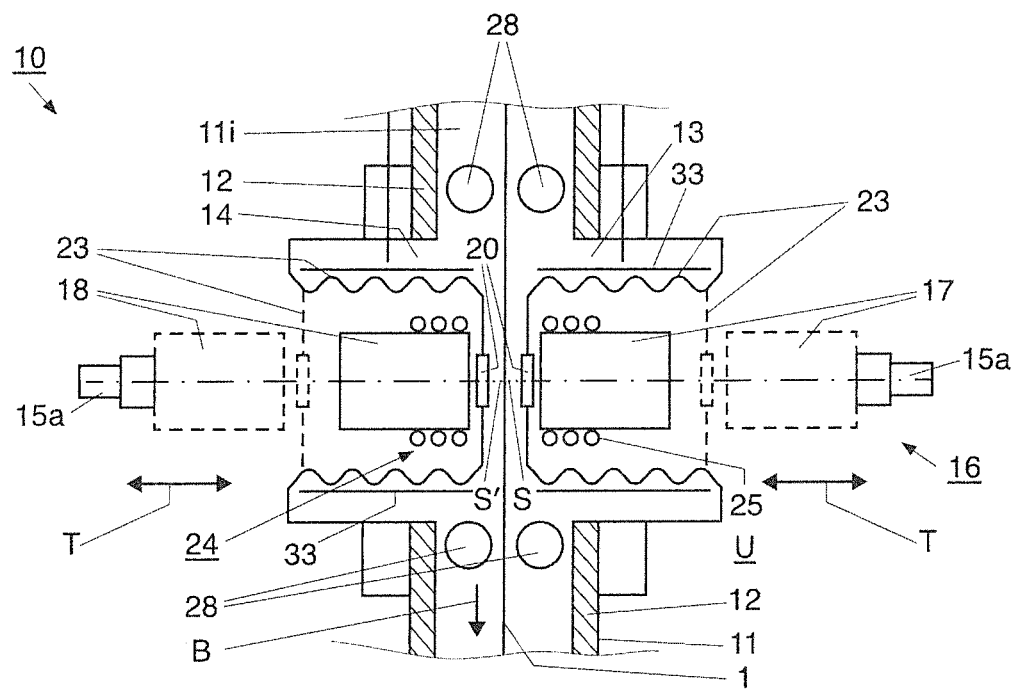
FIG. 5 shows a longitudinal sectional view of a housing of a device as described.

With reference to FIG. 5, which shows a longitudinal sectional view through the housing 11 of the device 10, further details will be described for the transmitting unit 17 or receiving unit 18, as the case may be, and the operating mechanism with respect to its possible movement relative to the wall 12 of the housing 11.

With the embodiment of FIG. 5, a metal product 1 can be moved through the housing 11 in a direction of movement B, specifically from top to bottom in the drawing plane of FIG. 5. The first opening 13 and the second opening 14 are formed in the wall 12 of the housing in such a manner that they are located on opposite sides of the metal product 1.

With respect to the two openings 13, 14 formed in the wall 12 of the housing 11, it is understood that the transmitting unit 17 is associated with the first opening 13, wherein the receiving unit 18 is associated with the second opening 14.

Accordingly, the transmitting unit 17 can be moved through the first opening 13 or adjacent thereto either into the interior space 11i of the housing 11 (in the drawing plane of FIG. 5 from right to left), or in the opposite direction thereto, specifically out of the interior space 11i in the direction to the outside (in the drawing plane of FIG. 5 from left to right). As already mentioned above, the transmitting unit 17 is operatively connected to an adjusting device 15a that, with the illustration shown here in FIG. 5, is attached to an outer end face of the transmitting unit 17 and is preferably of telescopic design. Thus, the actuation of the adjusting device 15a can move the transmitting unit 17 either into or out of the interior space 11i of the housing 11.

In the same manner, the receiver unit 18 is also connected at its outer end face to an adjusting device 15a, which is in particular of telescopic design. When this adjusting device 15a is actuated, the receiving unit 18 can be moved through the second opening 14 or adjacent thereto either into the interior space 11i of the housing 11 or in the opposite direction, specifically outwardly out of the housing 11.

Sealing devices 23, each formed of an elastically deformable material, are attached to the edges of the first opening 13 and the second opening 14. For example, such sealing devices 23 may be formed from a so-called "bellows." For the purposes of the following description, such a sealing device 23 will be referred to only briefly as a "bellows," without any limitation herein.

As a result of a respective bellows 23 being fastened to the edges of the respective openings 13, 14, the interior space 11i of the housing 11 at the location of such openings 13, 14 is sealed from its external surrounding area by the bellows 23.

Each bellows 23 is provided with a respective support structure 33 extending along a longitudinal extent of the bellows 23 (i.e., drawing plane of FIG. 5 horizontal in each case). Such a support structure 33 stabilizes a bellows 23 with respect to its lateral walls, in particular if the bellows 23 is moved, for example, far into the interior space 11i of the housing, as shown, for example, in the illustration of FIG. 5. In this regard, it is noted that, in the illustrations of FIGS. 5 and 6, such support structures 33 for the bellows 23 are only symbolically represented by horizontal lines for simplicity.

Figure 6:
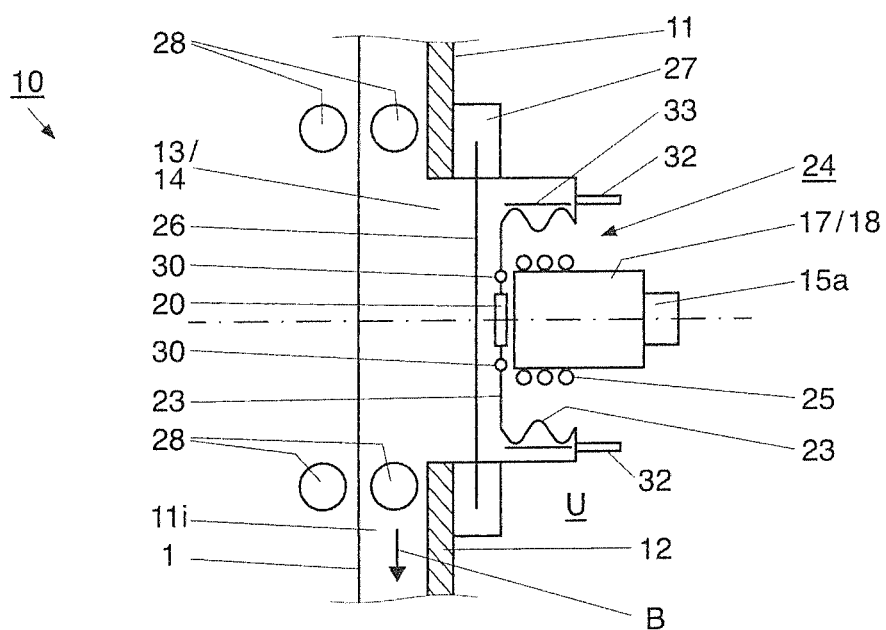
FIG. 6 shows an enlarged partial longitudinal sectional view of the illustration of FIG. 2.

FIG. 6 shows a partial longitudinal sectional view of the illustration of FIG. 5 and illustrates further details thereof. In view of a symmetry of the arrangement of components at the first opening 13 or the second opening 14, as the case may be, only one side of the housing 11 is shown in FIG. 6 for simplification. The illustration of FIG. 6 applies in the same manner to the first opening 13 as well as to the second opening 14, which is also expressed by the fact that the component of the measuring device 16 shown in FIG. 6 is designated by "17" or "18," because it is either the transmitting unit 17 or the receiving unit 18.

An outer end face of the bellows 23 is connected to adjusting means 32, with which a preferably translatory adjustment of the bellows 23 is possible, specifically either into the interior space 11i of the housing 11 or in the opposite direction, that is, out of the housing 11. In this context, it is pointed out that a movement or adjustment, as the case may be, of a respective bellows 23 by the adjusting means 32 connected thereto can take place independently of the adjusting device 15a or a movement of a component of the measuring device 16 (transmitting unit 17 and/or receiving unit 18), as the case may be.

With the embodiment of FIG. 5 or FIG. 6, as the case may be, a window 20 is integrated in each case on a front side of the individual bellows 23 facing the interior space 11i of the housing 11. When a bellows 23 is adjusted, a window 20 integrated therein is thus moved at the same time. Thus, the windows 20 in accordance with the embodiment of FIG. 5 or FIG. 6, as the case may be, are "wandering windows" whose respective spacing from the metal product 1 depends on the respective positioning of the associated bellows 23.

As already described above, the transmitting unit 17 is associated with the first opening 13, wherein the receiving unit 18 is associated with the second opening 14. As a result, the transmitting unit 17 can be moved into the interior space 11i of the housing 11, for example, through the first opening 13 by means of the actuation of the associated adjusting device 15a. Synchronized to this movement of the transmitting unit 17, it is understood that it is previously also the case that the bellows 23 on the right side of the metal product 1, which is fastened to the edges of the first opening 13 and thereby encloses the transmitting unit 17 along its outer periphery, has been moved into the interior space 11i of the housing 11 by an actuation of the adjusting means 32. Such positions for both the bellows 23 and the transmitting unit 17 on the right side of the metal product 1 are each shown by solid lines in FIG. 5.

In the same manner as the transmitting unit 17, the receiving unit 18 is also moved into the interior space 11i of the housing 11 with the illustration of FIG. 5, specifically by actuating the adjusting device 15a connected thereto. This is also accompanied by the fact that previously, or at least simultaneously, the bellows 23, which is arranged on the left side of the metal product 1 and encloses the receiving unit 18 along its outer periphery, has been moved into the interior space 11i of the housing 11 through the actuation of the adjusting means 32 connected therewith. Such positions for both the bellows 23 and the receiving unit 18 on the left side of the metal product 1 are also each shown by solid lines in FIG. 5.

For example, the positions in which both the transmitting unit 17 and the receiving unit 18 are each shown with solid lines in the illustration of FIG. 5 correspond to an operating position of such two components of the measuring device 16 in which they have been moved as close as possible to the metal product 1. In other words, a predetermined distance is set for at these positions between, on the one hand, the transmitting unit 17 or receiving unit 18, as the case may be, and, on the other hand, the strip-shaped metal product 1, which thus assumes the smallest possible value, for example approximately 10 mm.

The positioning of the transmitting unit 17 or receiving unit 18, as the case may be, in accordance with the illustration of FIG. 5 makes it clear that such components of the measuring device 16 are not arranged directly inside the interior space 11$i$ of the housing 11, but that, between them and the metal product 1, there is always the end face of an associated bellows 23 with a window 20 integrated therein.

The metal product 1, which with the embodiment of FIG. 5 or FIG. 6, as the case may be, is passed through the housing 11 of the device 10 along the direction of movement B, may be a strip-shaped material, for example cold strip or hot strip. Taking this into account, it is noted that a movement of the components of the measuring device 16 in FIG. 5 is respectively in a transverse direction, i.e., in a direction orthogonal to a surface of the strip-shaped metal product 1. Such a direction of movement is symbolized in FIG. 5 by a double arrow designated by "T."

At this point, it is separately pointed out that the two adjusting devices 15$a$, which are each operatively connected to the transmitting unit 17 and the receiving unit 18, can be actuated independently of each other. As a consequence, it is possible that such components 17, 18 of the measuring device 16 can also be moved independently of each other in the transverse direction T, in order to be moved into or out of the interior space 11$i$ of the housing 11.

In the illustration of FIG. 5, dashed lines indicate positions for both the components of the measuring device 16, i.e., the transmitting unit 17 and the receiving unit 18, and for the associated bellows 23, in which such elements have been moved out of the first opening 13 or the second opening 14, as the case may be. With respect to the bellows 23, such a movement between the positions shown in FIG. 5 by solid lines, on the one hand, and by the dashed lines, on the other hand, is made possible by the fact that such bellows 23 are formed of an elastically deformable material.

FIG. 6 shows the transmitting unit 17 or the receiving unit 18, as the case may be, in a position in which it has been moved out of the interior space 11$a$ in the transverse direction T through the actuation of the respective associated adjusting device 15$a$. In the same manner, the bellows 23 has been moved outward in this case, such that the window integrated in the end face of the bellows 23 is still located adjacent to the inner end face of the transmitting unit 17 or receiver unit 18, as the case may be.

Figure 15:
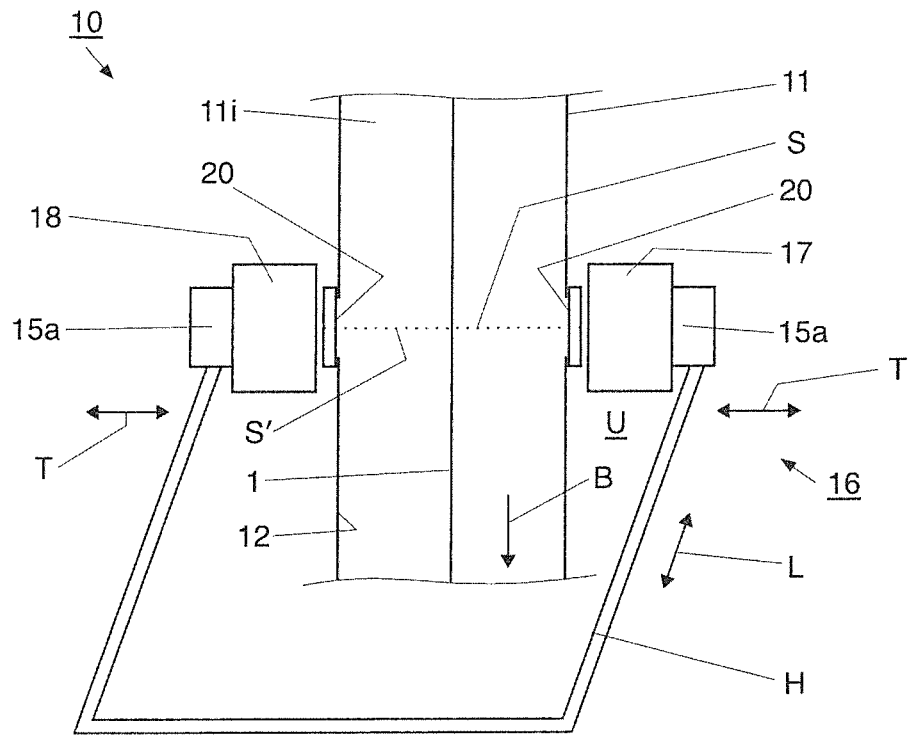
FIG. 15 shows a simplified side view of a device in accordance with a further embodiment.
Figure 16:
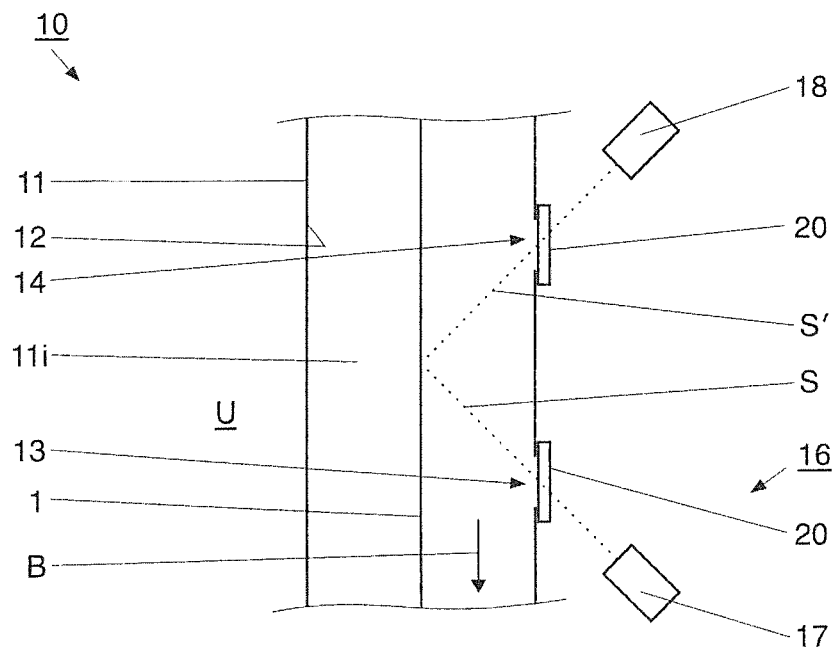
FIG. 16 shows a sectional view through a housing of a device in accordance with one embodiment, with which the components of an associated measuring device are arranged on the same side of the housing.

Adjacent to each of the two openings 13, 14, a closing device 26 is mounted on the housing 11 and is received in an associated container 27 or is slidably guided therein, as the case may be. If the components of the measuring device 16 (=transmitting unit 17 and receiver unit 18) are each located in the position shown in FIG. 6, a closing of the openings 13, 14, as shown in FIG. 6, and thus a sealing of the interior space 11 of the housing with respect to the surrounding area U, can be achieved by means of the closing device 26. As a consequence, it is possible, for example, to disassemble the bellows 23 from the opening 13, 14 and then to further remove the transmitting unit 17 or the receiving unit 18, as the case may be, from the housing 11, for example for repair and/or maintenance purposes, and/or also to implement a calibration or measurements of external samples that are not processed or treated, as the case may be, in the actual line for producing the metal product 1. Reference is also made to FIG. 15, which is described separately below.

Referring to the illustration of FIG. 6, cooling lines 30 may be integrated into the material of the bellows 23 at an end face thereof facing the interior space 11$i$, and preferably adjacent to the window 20. By passing a cooling fluid, preferably in the form of a cooling liquid, through such cooling lines 30, the end face of the bellows 23 is suitably cooled. This cooling at the end faces of a respective bellows 23 initially cools a window 20 integrated therein and can also have the effect of reducing thermal stress as a result of heat radiation acting on the component of the measuring device 16 (i.e., transmitting unit 17 or receiving unit 18, as the case may be) located on the opposite side of the window.

A further reduction in the thermal load for the transmitting unit 17 or receiving unit 18, as the case may be, can be achieved by providing a cooling device 24 for each of these, through which a coolant, preferably a cooling liquid, is passed for cooling the corresponding component of the measuring device 16. In the illustration of FIG. 5 or FIG. 6, as the case may be, such cooling device 24 can be in the form of a line coil 25 that is attached to an outer peripheral surface of the transmitting unit 17 or receiving unit 18, as the case may be.

Further cooling measures are described below in FIGS. 7 and 8.

Figure 7:
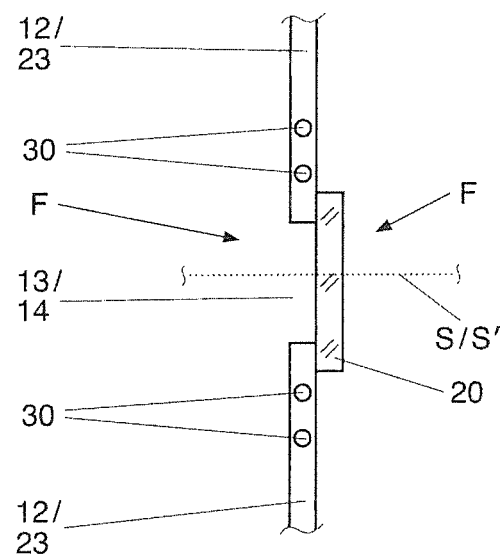
FIG. 7 shows a sectional view through a shield attached to a wall of the housing of the device or to a sealing device used for this purpose.

FIG. 7 shows a sectional view (longitudinal or cross-sectional) through a window 20, which can be fastened to a wall 12 of the housing 11 or to a bellows 23. Cooling lines 30 and/or cavities 30 are formed in the wall 12 of the housing 11 or in the material of the bellows 23, as the case may be, through which a cooling fluid, preferably a cooling liquid, is passed. This ensures that the material of the wall 12 or of a bellows 23, as the case may be, is cooled at least directly adjacent to the window 20, which also reduces the temperature load for such window 20 and also its temperature itself.

Figure 8:
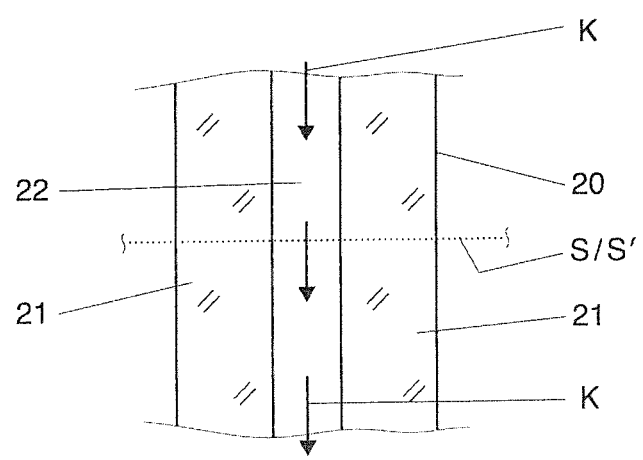
FIG. 8 shows a sectional view through a shield of FIG. 7, FIGS. 9-12 show respectively, longitudinal sectional views through a device in accordance with further embodiments, with a housing in accordance with FIG. 2.

FIG. 8 shows a section through a window 20 and illustrates a double-walled structure with which this window 20 is formed. In other words, such window comprises at least two surface elements that are spaced apart from each other and enclose a cavity 22 between them. A cooling fluid, preferably a cooling gas, can be passed through this cavity 22, thereby further cooling the window 20 and thereby reducing the amount of heat radiation that passes from the interior space 11$i$ of the housing 11 to the exterior through the window 20.

The device 10 also comprises a purge gas device having nozzles from which a purge gas can be dispensed onto the surface of a window 20. This is symbolically indicated in FIG. 7 by the two arrows, each designated by "F." The nozzles of the purge gas device may be arranged in the interior space 11$i$ of the housing 11 and/or on the outer side of the housing 11, preferably adjacent to the first opening 13 or the second opening 14, as the case may be.

With respect to the functional mechanism according to which, in accordance with the illustration in FIGS. 5 and 6, it is possible to move the components of the measuring device 16 in the transverse direction T, it is understood that this functional mechanism is possible with the associated arrangement of the transmitting unit 17 and receiving unit 18 in the region of the respective openings 13, 14 for one of the housing shapes shown in FIGS. 1-4. For example, with regard to one of FIGS. 2-4, it may be emphasized that an arrangement of the components of the measuring device 16 in accordance with the illustration of FIGS. 5 and 6 is also possible, in particular, in the region of a narrow point 19 of the housing 11 at which the two openings 13, 14 are formed.

With reference to FIG. 5, the device functions as follows:

During its metallurgical production, the metal product 1 is passed through the housing 11 of the device 10 along the direction of movement B. In an operating position of the device 10, the transmitting unit 17 and receiver unit 18, and synchronized to this also the associated bellows 23, are each moved in the transverse direction T into the interior space 11i of the housing 11, as shown in FIG. 5 in each case by solid lines and already described above. Thereby, the bellows 23 with the windows 20 integrated therein are moved as close as possible to the metal product 1, such that the transmitting unit 17 and the receiver unit 18 can be arranged at a predetermined distance from the metal product 1, which is also as close as possible, for example approximately 10 mm.

The transmitting unit 17 is designed in such a manner that it generates an electromagnetic field, for example in the form of X-ray radiation. The resulting electromagnetic radiation, designated by S in FIG. 5, passes from the transmitting unit 17 initially through the window 20 of the associated bellows 23 and then through the metal product 1. In FIG. 5, S' designates the wave pattern that remains and/or results on the other side of the metal product 1 after passing through it and is then received by the receiving unit 18 after passing through the window 20 of the bellows 23, which surrounds the receiving unit 18.

If the transmitting unit 17 and the receiving unit 18 of the device 10 are arranged on opposite sides of the metal product 1 in accordance with the illustration of FIG. 5, the determination of at least one property of the metal product 1 can be based on the transmission or penetration principle, for example in the case of X-ray radiation.

In accordance with an alternative embodiment, it is also possible that the components 17, 18 of FIG. 5 may each be IMPOC measuring heads. This also applies in the same manner to the embodiments according to FIGS. 9-15 and FIGS. 19 and 24, which are described further below.

At this point, it may be pointed out once again that the windows 20, which are integrated into the respective bellows 23, are transparent with respect to the waves of electromagnetic radiation, preferably X-ray radiation or laser radiation, or with respect to the field lines of the electromagnetic field generated by the transmitting unit.

The receiver unit 18 is connected in terms of signal technology to an evaluation unit (not shown). By means of such evaluation unit, the remaining and/or resulting part of the physical interaction, for example in the form of a wave pattern of the transmitted X-ray radiation, which has been received or detected, as the case may be, by the receiving unit 18, is then suitably evaluated and, on the basis thereof, at least one property or material parameter, as the case may be, for the metal product 1 is determined.

Even during the metallurgical production of the metal product 1, the distance between the components (=transmitting unit 17 and/or receiving unit 18) of the measuring device 16 and the metal product 1 can be set or targeted to a predetermined distance by moving the transmitting unit 17 and/or the receiving unit 18 in the transverse direction T. For example, this can be done in adaptation to a changed thickness of the metal product 1.

At this point, it is pointed out that the functional mechanism described with respect to FIG. 5, by means of which the components 17, 18 of the measuring device can be moved adjacent to the openings 13, 14 of the housing 11 using the bellows 23 stabilized, if necessary, by the use of the supporting structures 33, can also be used in other embodiments of the device 10.

Further features and embodiments of the device 10 are described below:

The device 10 comprises a protective sliding device 28 (see FIG. 5, FIG. 6) arranged within the interior space 11i of the housing 11. This protective sliding device 28 fulfills a safety function and ensures sufficient spacing of the metal product 1, if it is passed through the housing 11 in the direction of movement B, from the openings 13, 14 and/or from the components of the measuring device 16 and/or from the bellows 23. For example, the protective sliding device 28 prevents the metal product 1 from coming into contact with the end faces of the respective bellows 23 and the windows 20 integrated therein as a result of possible lateral movement in the direction of one of the side walls of the housing 11. Accordingly, possible damage to the bellows 23 and the components of the measuring device 16 arranged behind it by the metal product 1 can be prevented thanks to the protective sliding device 28.

Figure 13:
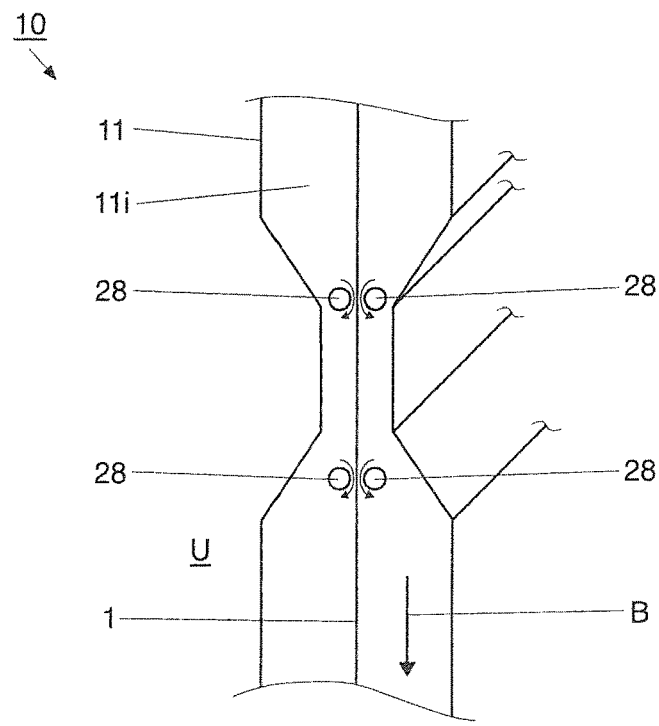
FIG. 13 shows a perspective view through the housing of a device in accordance with a further embodiment.

The embodiment of FIG. 13 illustrates that the protective sliding device has respective guide rollers that are rotatably supported and may be in contact with the metal product 1, during which the metal product 1 is guided through the housing 11 in the direction of movement B. This rolling contact between the guide rollers 28 and the metal product 1 provides defined guidance for the metal product 1 within the interior space 11i of the housing 1, wherein possible deflections of the metal product 1 to the side are less likely if not impossible. As already described above, this can prevent the metal product 1 from unintentionally coming into contact with the end faces of the bellows 23 and damaging them or the components of the measuring device 16 arranged behind it, as the case may be.

Figure 14:
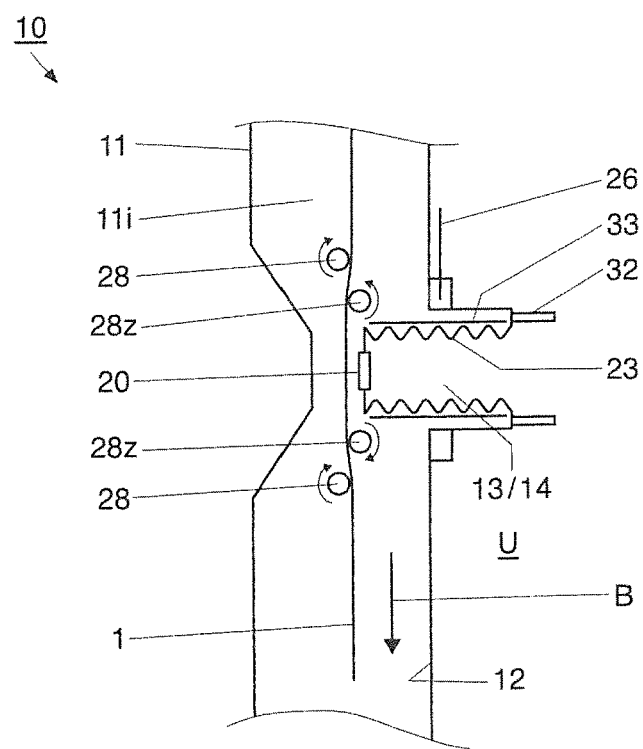
FIG. 14 shows a perspective view through the housing of a device in accordance with a further embodiment.

FIG. 14 shows an additional variant with respect to the guide rollers 28 of the protective sliding device in connection with a shape of the housing 11 in accordance with FIG. 2. With the embodiment of FIG. 14, the transmitting unit 17 and the receiving unit 18 may be arranged in the openings 13, 14, which are formed in opposite sides of the housing 11 according to the operating mechanism in accordance with FIG. 5.

In the variant in accordance with FIG. 14, two guide rollers 28z can be moved in the direction of an opposite wall of the housing 11, preferably in a translatory manner, in order to thereby come into contact with the metal product 1 and, if necessary, exert a compressive force on the metal product 1. In the illustration of FIG. 14, such movable guide rollers 28z are arranged on the right side of the metal product 1. Such movable guide rollers 28z have a smaller distance to each other than two additional guide rollers 28, which are arranged on the opposite side of the metal product (in FIG. 14 on the left side). Now, if the movable guide rollers 28z, with respect to the drawing plane of FIG. 14, are moved from right to left, it is thus achieved that the strip-shaped metal product 1 is guided in a defined manner between, on the one hand, the movable guide rollers 28z and, on the other hand, the two guide rollers 28 arranged on the other side of the metal product 1 within the interior space 11i of the housing 11, such that there is no danger of the metal product 1 deflecting to the side with an undesired contact with the bellows 23. Furthermore, the targeted positioning of the movable guide rollers 28z against the strip-shaped metal product 1 results in a compressive force being exerted on the metal product 1, which then causes a tensile force in a longitudinal extension of the metal product 1. In this manner, a possible "flapping" of the strip-shaped metal product 1 can be prevented, in order to thereby also exclude a possible damage of the bellows 23 or the components of the measuring device 16 arranged behind it, as the case may be.

With the aid of the protective sliding device in accordance with FIG. 14, with which two movable and rotatably mounted guide rollers 28z are set against the strip-shaped metal product 1 as described, it is achieved that the metal product 1 is selectively guided within the interior space 11i of the housing at least in the region adjacent to the openings 13, 14. Accordingly, an end face of a bellows 23, which is associated with the transmitting unit 17 or the receiving unit 18, and thus also the associated component 17, 18 of the measuring device 16, can then be arranged even closer to the metal product 1, for example at a distance of less than 10 mm, since, as a result of the targeted guidance of the metal product 1, there is no risk of lateral "flapping" and thus damage to the bellows 23 and the components 17, 18 of the measuring device 16 arranged behind it.

With reference to FIG. 14, it may be additionally pointed out that, for the purpose of a simplified illustration, and because of the present axial symmetry of the housing 11 in the vertical direction shown here, a bellows 23 is shown only on one side of the housing 11 and without a component 17, 18 of the measuring device 16 enclosed thereby. Furthermore, it can be seen that, in FIG. 14, a bellows 23 is moved into the interior space 11i of the housing 11 in such a manner that its end face facing the interior space 11i with the window integrated therein is positioned directly adjacent to the metal product 1. It can also be seen that the distance between the two movable guide rollers 28z is selected to be so large that there is room for the bellows 23 between such guide rollers 28z when it is positioned in close proximity to the metal product 1.

FIG. 15 shows an embodiment of the device 10 in a simplified side view with which the components of the measuring device 16, i.e., the transmitting unit 17 and the receiving unit 18, can be arranged adjacent to the two openings 13, 14 in the same manner as in the functional mechanism of FIG. 5.

It can be seen from FIG. 15 that the device 10 also comprises a holding device H to which the transmitting unit 17 and the receiving unit 18 are jointly attached. Thus, the holding device H forms a frame device that, for example and in accordance with the illustration of FIG. 15, is C-shaped. With this holding device H, the transmitting unit 17 and the receiving unit 18 may be movably adjusted in a longitudinal direction L parallel to a surface of the strip-shaped metal product 1. Specifically, this means that the transmitting unit 17 and the receiving unit 18, if they have previously been moved sufficiently far out of the interior space 11i of the housing 11 in the transverse direction (see FIG. 6), can then subsequently be moved away from the housing 11 in the longitudinal direction L, that is, far away, by means of the holding device H, and thus "driven out of line."

If the transmitting unit 17 and receiving unit 18 have been moved sufficiently far away from the housing 11 by means of the holding device H by a movement in the longitudinal direction L as just described, it is possible to use the measuring device 16 with such components 17, 18 for other measurements, for example for measuring calibrated or gauged sample bodies for the purpose of calibrating the components 17, 18 of the device 10. Additionally, or alternatively, for the present invention, maintenance and/or repair work can be provided for the components 17, 18 of the device 10 after the transmitting unit 17 and the receiving unit 18 have been removed from the housing 11 by a movement in the longitudinal direction by means of the holding device H, as described.

In FIGS. 9 to 12, additional embodiments for the device 10 are shown, specifically in each case in a longitudinal sectional view through the housing 11. The common feature for such embodiments is that a housing type in accordance with FIG. 2, with which the housing 11 has a narrow point 19 in the region of the openings 13, 14, is used for this purpose. Furthermore, the transverse direction in which the transmitting unit 17 and the receiving unit 18 are movable relative to the housing 11 by means of an adjusting device 15a connected thereto is indicated herein in the same manner as in FIG. 5 by an arrow designated by "T" in each case.

Figure 9:
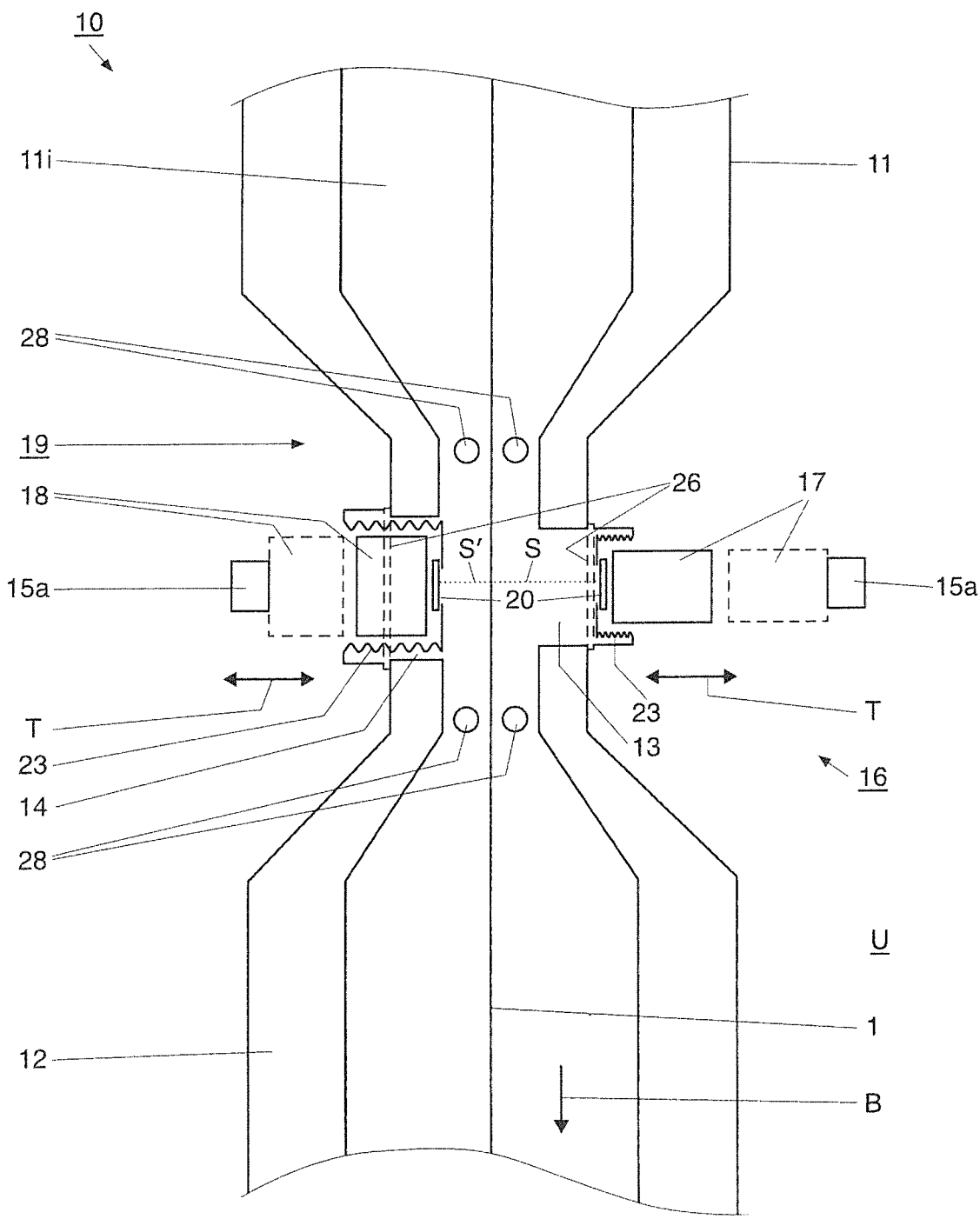

With the embodiment according to FIG. 9, the transmitting unit 17 and the receiving unit 18 may be movably mounted in the region of the openings 13, 14 formed in the wall 12 of the housing 11 according to the same functional mechanism as in FIG. 5, wherein the sealing of the interior space 11i of the housing is achieved by using the bellows 23.

The illustration of FIG. 9 further clarifies that the two openings 13, 14 can each be closed by a closing device 26, symbolized here in each case only by a dashed line, if the components 17, 18 of the measuring device 16 have been moved sufficiently far out of the interior space 11 of the housing. This can be done in the same manner as in FIG. 6, where such a closing device 26 is shown and has already been described.

Figure 10:
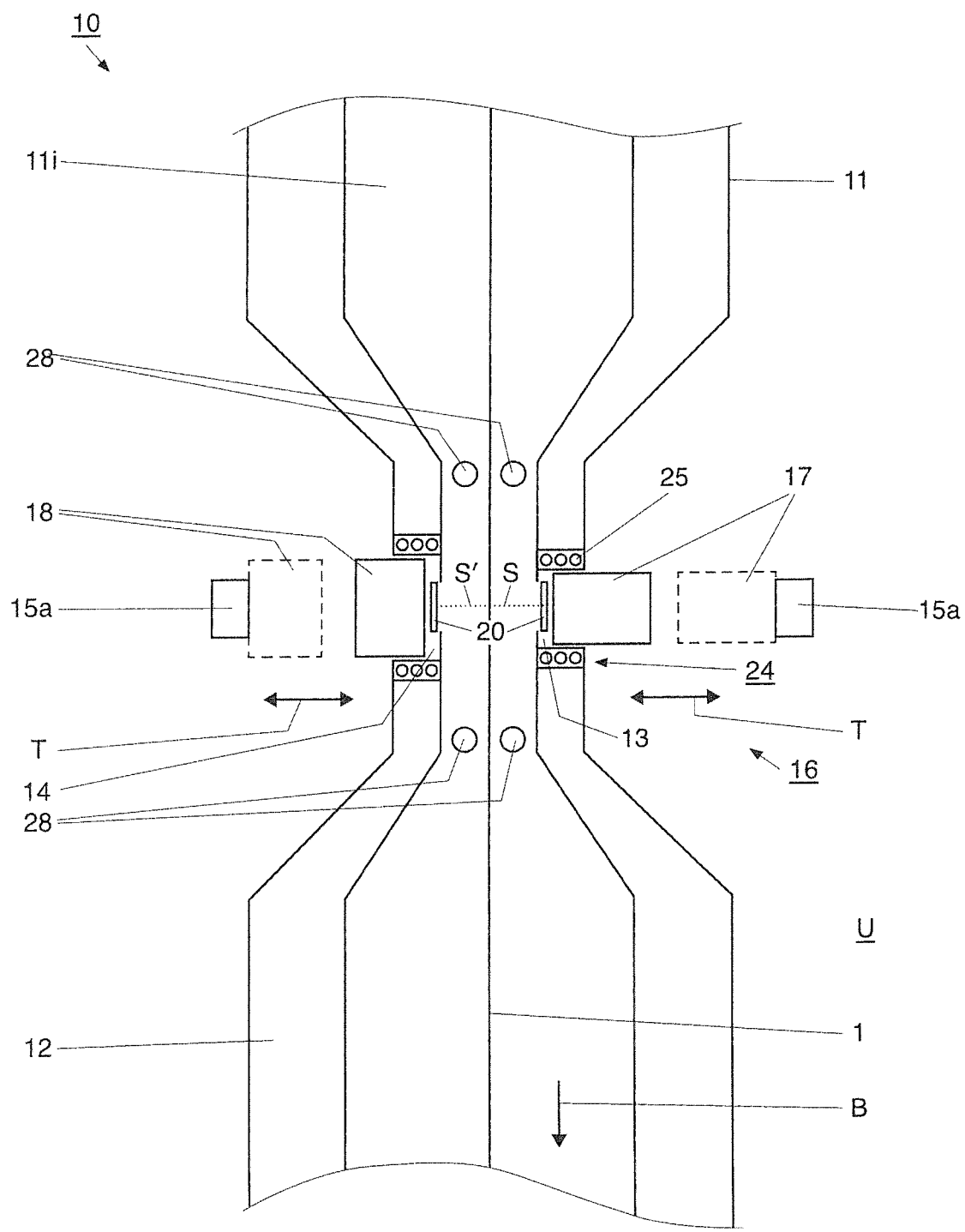

With the embodiment of FIG. 10, no bellows are used to seal the interior space 11i; this is because the windows 20 are attached directly to the housing 11 adjacent to the first opening 13 and to the second opening 14, and in this respect sealing of the interior space 11i is ensured. Furthermore, the illustration of FIG. 10 illustrates that cooling channels 25 are formed in the housing 11i adjacent to each of the two openings 13, 14, in order to cool the housing 11 immediately adjacent to the windows 20 attached thereto.

With the embodiments in accordance with FIG. 9 and FIG. 10, the transmitting unit 17 and the receiving unit 18 are each shown by dashed lines in a position in which they are completely moved both out of the interior space 11i of the housing 12 and out of the openings 13, 14 associated with them—starting from this position, such components of the measuring device 16 can then be moved away from the housing 11 in the described manner in the longitudinal direction L by means of the holding device H (see FIG. 15), which for simplicity is not shown in FIGS. 9-12.

Figure 11:
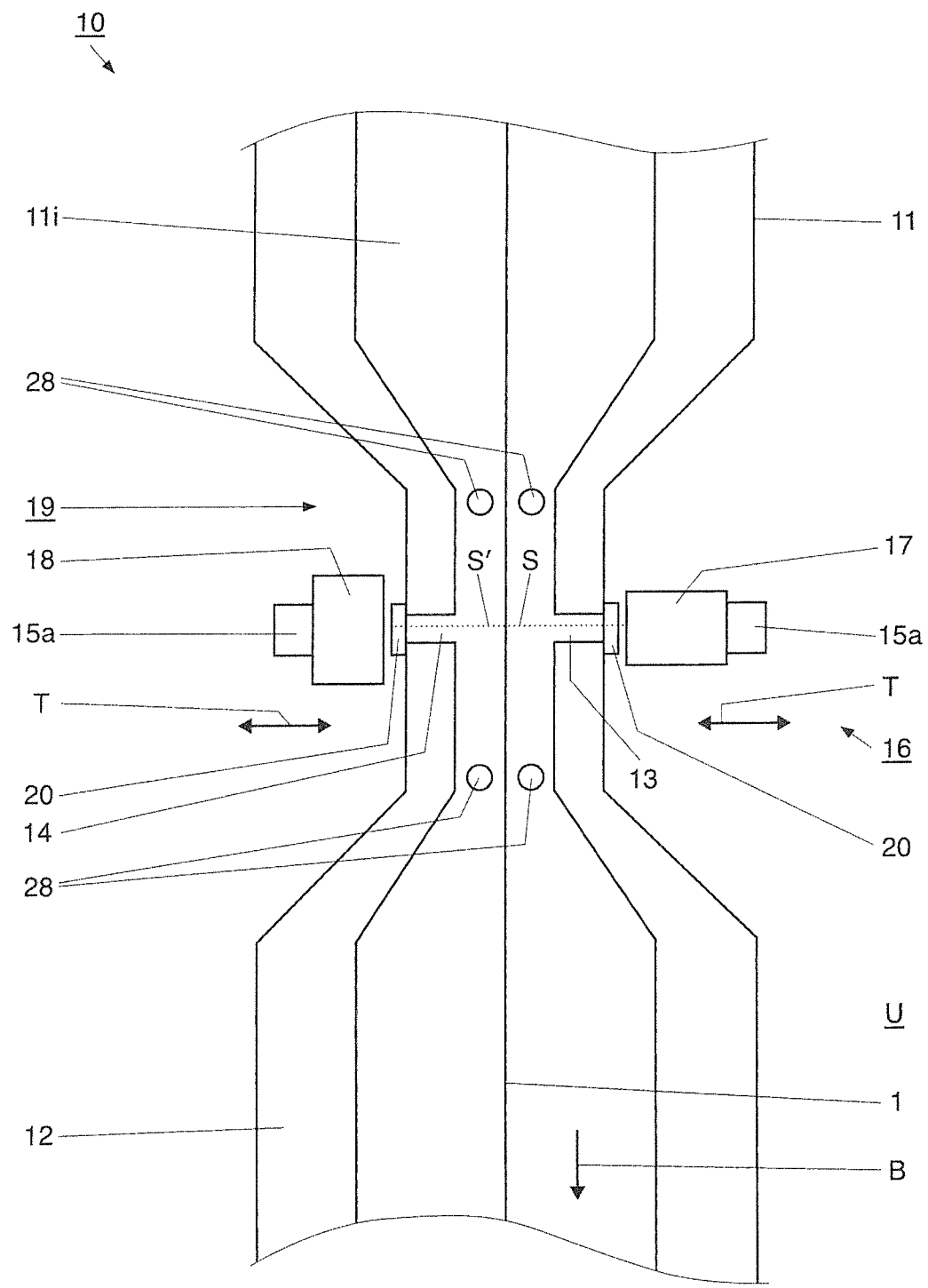
Figure 12:
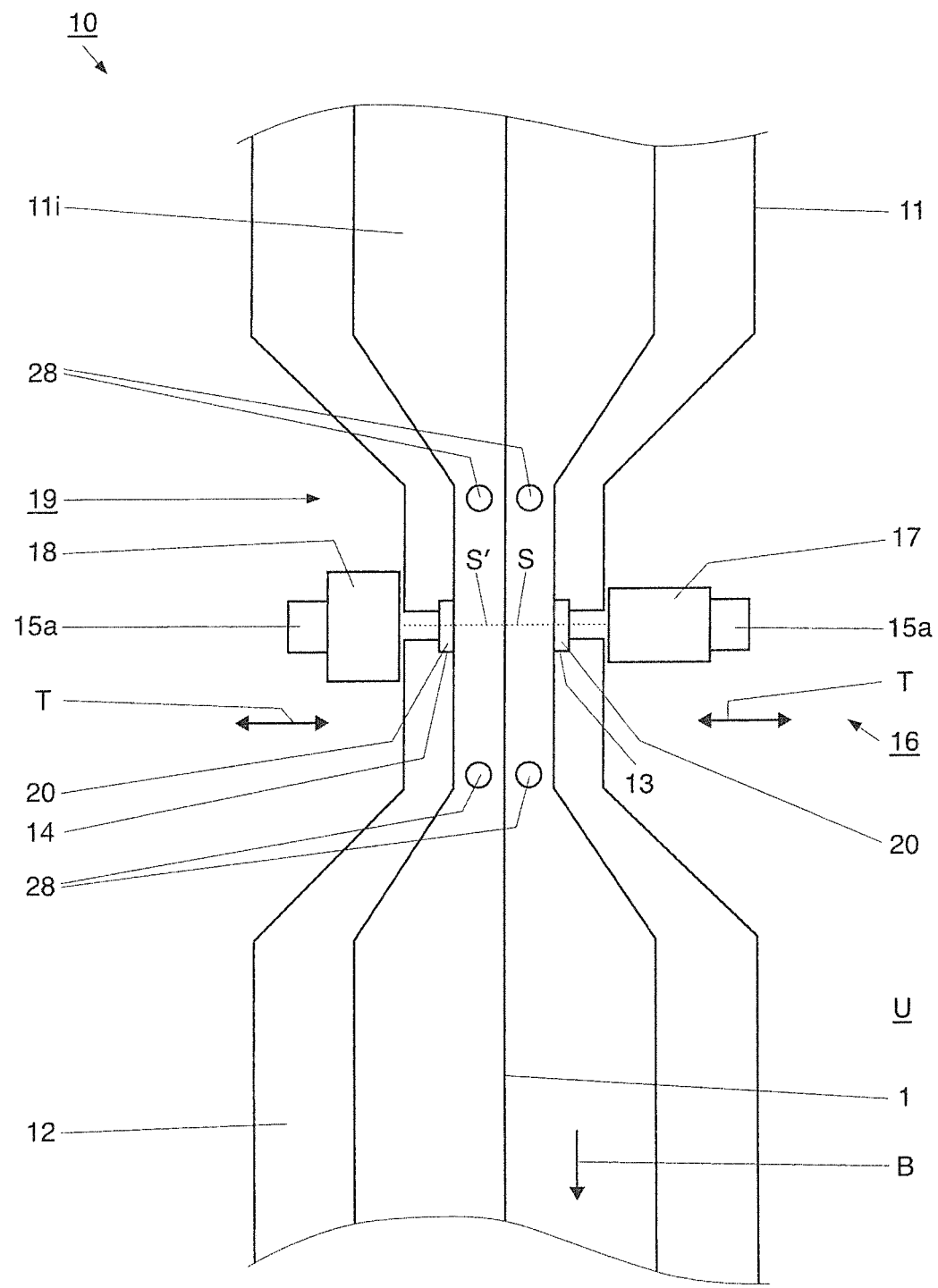

With the embodiments of FIG. 11 and FIG. 12, the windows 20, in the same manner as with the embodiment of FIG. 10, are attached directly to the housing 11 and adjacent to the openings 13, 14. In this respect, such embodiments also do not require the use of a bellows in order to achieve the sealing of the interior space 11i with respect to the surrounding area U.

All of the embodiments specified above in accordance with FIGS. 1-15 have in common that, thereby, the components of the measuring device 16, that is, the transmitting unit 17 and the receiving unit 18, are arranged on opposite sides of the metal product 1 in each case. As a result, with these embodiments of the invention, the waves generated by the transmitting unit 18, for example of electromagnetic radiation, preferably X-ray radiation, pass through the metal product 1 in each case, which is symbolized in each case by a dotted line designated by S in the specified figures. The remaining and/or resulting wave pattern, symbolized in each of the specified drawings by a dotted line designated by S', is then received on the opposite side of the metal product 1 by the receiving unit 18.

FIGS. 17 to 25 show additional embodiments. Thereby, the sealing concept for the interior space 11*i* of the housing 11 in connection with a mobility of the components 17, 18 of the measuring device 16 relative to the housing 11 is also implemented using bellows 23 with windows 20 integrated therein, wherein such bellows 23—in the same manner as already described for FIG. 5—are fastened to the edges of the openings 13, 14. All bellows 23 of the embodiments in accordance with FIGS. 17-25 are connected to adjusting means, with which it is possible to move such bellows 23 into the interior space 11*i* of the housing 11 and also in the opposite direction, that is, out of the housing 11. For simplicity, such adjusting means is not shown in FIGS. 17-25. For example, it is also possible to move such bellows 23 independently of each other and in particular in the case where the associated components 17, 18 of the measuring device 16 are each located outside the housing 11 of the device 10.

Figure 17:
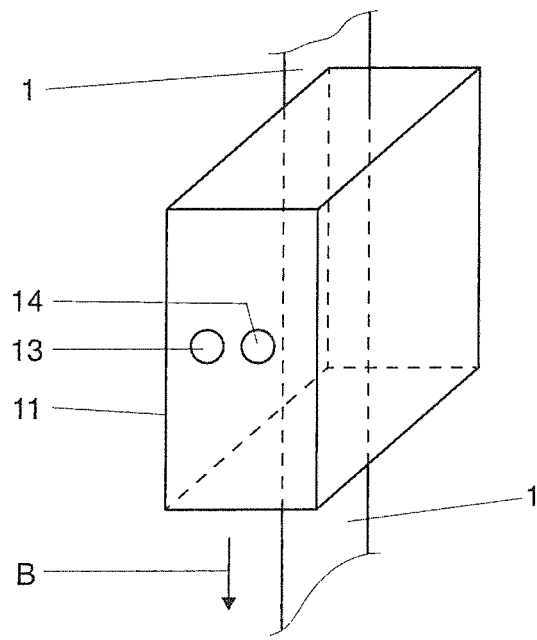
FIGS. 17-19 shows various views of details of a device in accordance with a still further embodiment.
Figure 18:
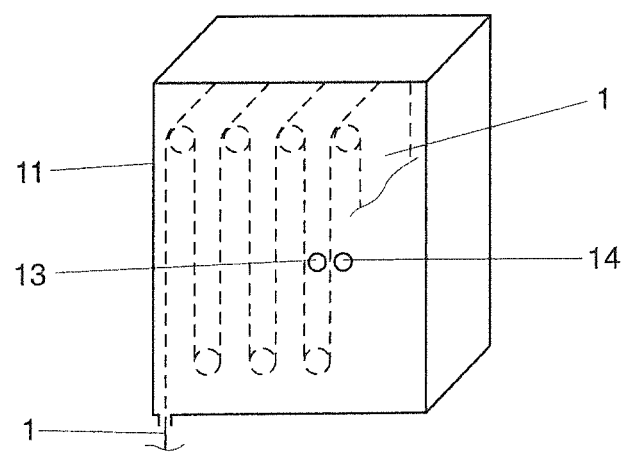

With the embodiments according to FIG. 17 and FIG. 18, the device 10 comprises in each case a housing 11, with which the two openings 13, 14 are formed side by side in a wall 12, which is arranged in alignment with the surface of the strip-shaped metal product 1. Thereby, in the perspective views in accordance with FIG. 17 and FIG. 18, both the strip-like formation of the metal product 1 and the direction of movement B, in which the strip-like metal product 1 is moved through the housing 11 of such embodiments, are shown.

Figure 19:
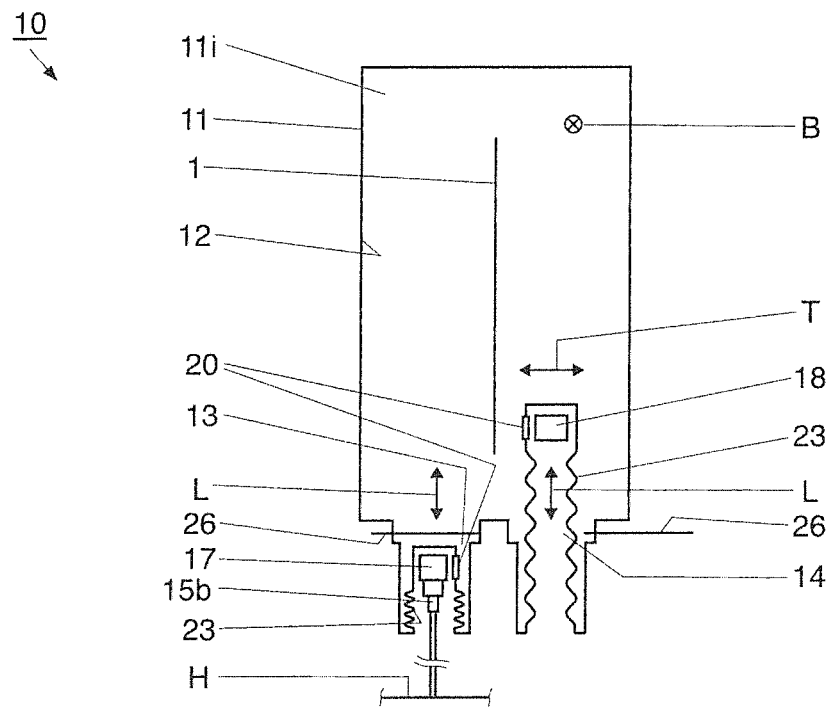

The illustration of FIG. 19 shows a cross-section of the housing 11 of FIG. 17. As just described, in this case the first opening 13 and the second opening 14 are formed side by side in a same wall 12 of the housing 11, wherein the transmitting unit 17 is associated with the first opening 13 and the receiving unit 18 is associated with the second opening.

In the same manner as with the previous embodiments, with the embodiment of FIG. 19 the transmitting unit 17 and the receiving unit 18 are each operatively connected to adjusting devices, which are here designated by "15*b*" and can be actuated independently of one another, as already described. For the sake of a simplified illustration, the adjusting device for the receiver unit 18 is not shown in FIG. 19.

With respect to the strip-shaped configuration of the metal product 1, the transmitting unit 17 and/or the receiving unit 18 are moved in the longitudinal direction L, that is, parallel to a surface of the strip-shaped metal product 1, upon actuation of an adjusting device 15*b* associated therewith, and thereby can be moved either into the interior space 11*i* of the housing 11 or out of the housing 11.

With reference to the illustration of FIG. 19, the following additional aspects are noted:

The transmitting unit 17 and the receiving unit 18 are shown by way of example and in comparison with each other in various operating positions: The transmitting unit 17 is located adjacent to the first opening 13 and outside the interior space 11*i* of the housing 11, whereas the receiving unit 18 is moved in the longitudinal direction L into the interior space 11*i* of the housing 11.

Windows 20 are integrated in lateral regions of the bellows 23, which are respectively associated with and enclose the transmitting unit 17 and the receiver unit 18, in the same manner as already described for FIG. 5.

Adjacent to the two openings 13, 14—in the same manner as already described for FIG. 6—closing devices 26 are attached to the housing 11. If the components 17, 18 of the measuring device 16 are arranged outside the interior space 11*i* of the housing 11, an opening 13, 14 can be closed by an associated closing device 26. In FIG. 19, this is the case for the first opening 13.

If the closing device 26 associated with the first opening 13 is transferred to its open position, as is the case in FIG. 19 for the closing device 26 associated with the second opening 14, the transmitting unit 17 can be moved into the interior space 11*i* of the housing 11 through the actuation of the adjusting device 15*b* in the longitudinal direction L, for example into the position in which the receiving unit 18 is also shown. In this respect, it is understood that the bellows 23, which encloses the transmitting unit 17, is either moved synchronously with the transmitting unit 17 or has previously been moved into the housing 11.

With respect to the receiving unit 18 as well and with respect to the position shown in FIG. 19, it is understood that the associated bellows 23 has been moved either synchronously with the receiving unit 18 or previously.

If the transmitting unit 17 has also been transferred to the position in which the receiving unit 18 is shown in FIG. 19 by moving in the longitudinal direction L, these two components 17, 18 of the measuring device 16 are then respectively arranged on opposite sides of the strip-shaped metal product 1, where the windows 20 integrated in the associated bellows 23 respectively face the strip-shaped metal product 1. Accordingly, at least one property of the metal product 1 can then be determined according to the transmission or penetration principle, in the same manner as already described for FIG. 5.

After the transmitting unit 17 and/or the receiving unit 18 have been moved into the interior space 11*i* of the housing 11 as corresponding to the position shown for the receiving unit 18, it is possible to move the transmitting unit 17 and/or the receiving unit 18 in the transverse direction T by a corresponding actuation of the adjusting device 15*b* as well, in order to thereby selectively change the distance to the metal product 1 and set it to a predetermined value.

The adjusting devices 15*b*, which are assigned to the transmitting unit 17 and the receiving unit 18, are attached to a holding device L—in the same manner as the adjusting device 15*a* with the embodiment of FIG. 15. For simplicity, this is shown in FIG. 19 only for the adjusting device 15*a* connected to the transmission unit 17. If the transmitting unit 17 and receiving unit 18 are each located outside the housing 11 and are far enough away from the openings 13, 14 of the housing 11, it can be achieved by means of an actuation of the holding device H that the transmitting unit 17 and receiving unit 18 are removed from the housing 11, for example in the transverse direction T, in order to carry out, for example, a calibration measurement and/or maintenance or repair work as the case may be, at another location.

And finally: The direction of movement B for the strip-shaped metal product 1 extends into the drawing plane in the illustration of FIG. 19.

Figure 20:
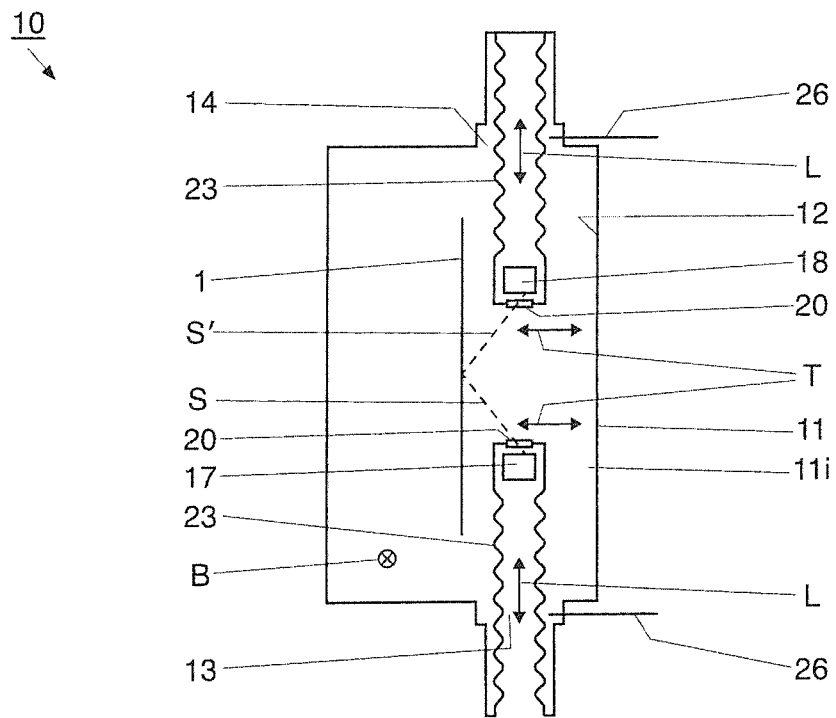
FIG. 20 shows a cross-sectional view through the housing of a device in accordance with a variant of FIG. 19, FIGS. 21-22 show various views of details of a device in accordance with a still further embodiment.

The embodiment of FIG. 20 comprises a housing 11 similar to that of FIG. 17, with the difference that thereby the first opening 13 and the second opening 14 are not formed in the same wall 12, but in opposite walls 12 of the housing. With the proviso that, with the embodiment of FIG. 20 as well, the transmitting unit 17 is assigned to the first opening 13 and the receiving unit 18 is assigned to the second opening 14, the functional mechanism by which it is possible to move the components 17, 18 of the measuring device 16 in the longitudinal direction L into the interior space 11i of the housing 11 or in the opposite direction, that is, out of the housing 11, and to close the interior space 11i by means of the closing devices 26, corresponds to that of FIG. 19, such that, for the avoidance of repetitions, reference may be made to the descriptions for FIG. 19. It is additionally noted that, with the illustration of FIG. 20, the adjusting device 15b and the holding device L, which can be designed in the same manner as with the embodiment of FIG. 15, are not shown for the purpose of a simplified illustration.

The embodiment in accordance with FIG. 20 is characterized in that the transmitting unit 17 and the receiving unit 18, when moved into the interior space 11i of the housing 11 in accordance with the illustration of FIG. 20, are then arranged on the same side of the strip-shaped metal product 1. Accordingly, a determination of at least one property of the metal product 1 is performed according to the reflection principle, by directing the waves of an electromagnetic radiation S generated by the transmitting unit 17 through the window 20 of the bellows 23 onto the metal product 1, wherein the remaining and/or resulting wave pattern S' are then received by the receiving unit 18. In all other respects, with the embodiment of FIG. 20, the direction of movement B for the strip-shaped metal product 1 corresponds to that of FIG. 19 and extends into the drawing plane.

Figure 21:
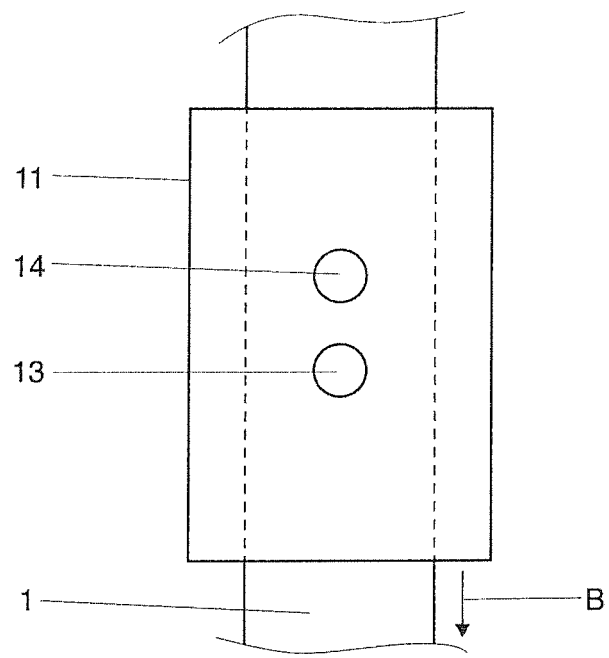

The embodiment of FIG. 21 comprises a housing 11 in which the first and second openings 13, 14 are formed in the same wall 12. Such housing 11 is designed such that a strip-shaped metal product 1 is passed vertically therethrough, as symbolized for the side view of FIG. 21 by the arrow B for the direction of movement of the metal product 1.

Figure 22:
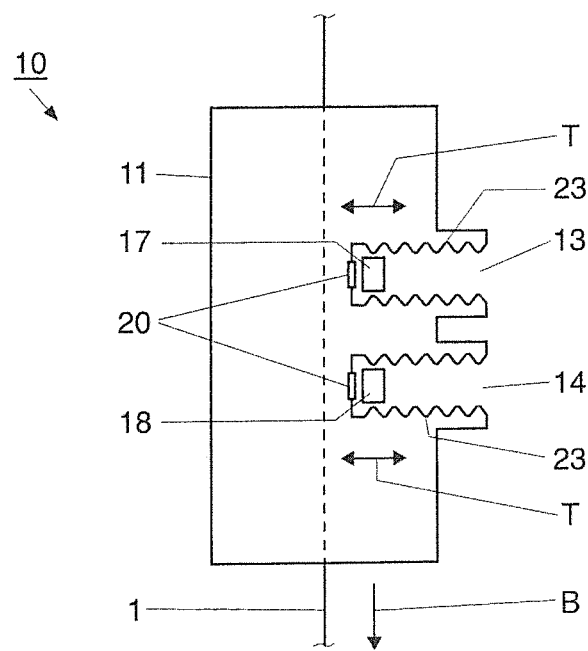

FIG. 22 shows the housing 11 of FIG. 21 in a longitudinal sectional view.

With the embodiment in accordance with FIG. 21 and FIG. 22, the principle that the transmitting unit 17 is assigned to the first opening 13 and the receiving unit 18 is assigned to the second opening 14 is also followed. The functional mechanism for moving such components 17, 18 of the measuring device 16 in the region of the openings 13, 14 and also for moving the bellows 23 corresponds in the same manner to the embodiment of FIG. 19, such that reference is made to the descriptions for FIG. 19 in order to avoid repetition.

The illustration of FIG. 22 shows the transmitting unit 17 and the receiver unit 18 each in a position in which they are moved into the interior space 11i of the housing 11. The transmitting unit 17 and the receiving unit 18 reach such position by being moved in the transverse direction T through the actuation of the respective associated (and not shown here) adjusting devices. FIG. 22 illustrates the fact that the transmitting unit 17 and the receiving unit 18 are each arranged on the same side of the strip-shaped metal product 1 in such positions. Accordingly, during the operation of the device 1 and the associated measuring device 16, the determination of at least one property of the strip-shaped metal product 1 is carried out according to the reflection principle, in the same manner as with the embodiment in accordance with FIG. 20.

In addition to FIG. 22, it is pointed out that a common adjusting device 15b can be provided for the transmitting unit 17 and the receiving unit 18, with which a movement of such components 17, 18 of the measuring device 16 in the transverse direction is then realized.

Figure 23:
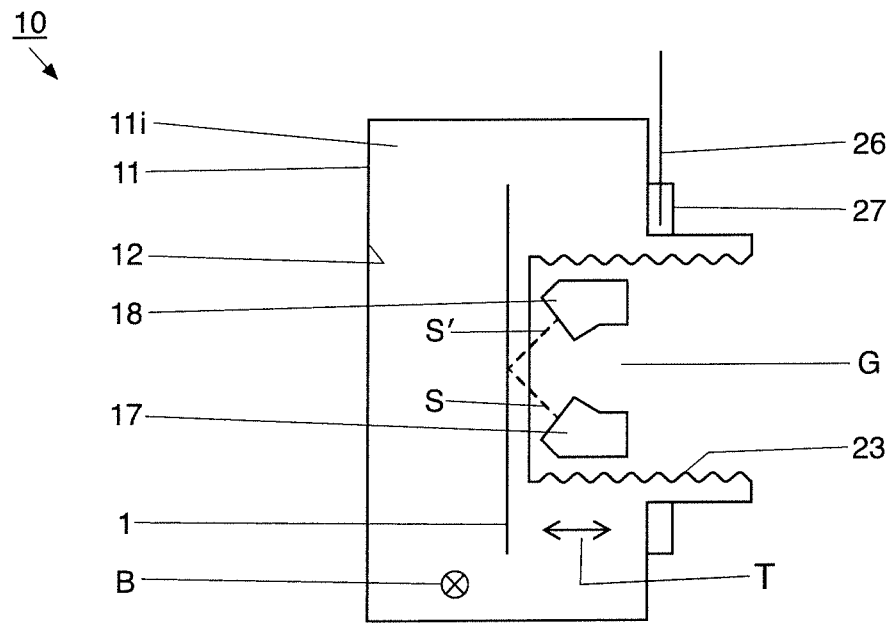
FIG. 23 and FIG. 24 show details of devices in accordance with yet further embodiments.

The embodiment of FIG. 23 corresponds to a variant of the embodiment in accordance with FIG. 21 or FIG. 22, as the case may be, with the modification that, here, the two openings 13, 14 are not formed separately from each other and one above the other in the same wall 12 of the housing 11, but are instead combined in a common opening G. This can be seen in the illustration of FIG. 23, which shows a cross-sectional view through the housing 11.

In the illustration of FIG. 23, the transmitting unit 17 and the receiving unit 18 are each shown in a position when they are moved in the transverse direction T into the interior space 11i of the housing. Thereby, it can be seen that the components 17, 18 of the measuring device 16, in the same manner as in FIG. 20, are arranged on the same side of the strip-shaped metal product 1, such that, during the operation of the measuring device 16, at least one property of the strip-shaped metal product is determined according to the reflection principle.

In view of the fact that, with the embodiment of FIG. 23, the components 17, 18 of the measuring device 16 can be moved through the common opening G of the housing 11, it is also expedient to use only one adjusting device (not shown in FIG. 23) with which the transmitting unit 17 and the receiving unit 18 are operatively connected in order to implement this movement.

With the embodiment of FIG. 23, a common bellows 23 is preferably provided for the transmitting unit 17 and receiving unit 18, wherein such bellows 23 is attached to the edges of the opening G and is movable relative to the opening G of the housing 11 and in the transverse direction T by means of an associated adjustment unit. On one end face of such common bellows 23, which faces the strip-shaped metal product 1, a window (not shown) is integrated in the same manner as in FIG. 22, which window is transparent with respect to the waves of electromagnetic radiation as described, in order to enable the measurement of the metal product 1 according to the reflection principle.

Figure 24:
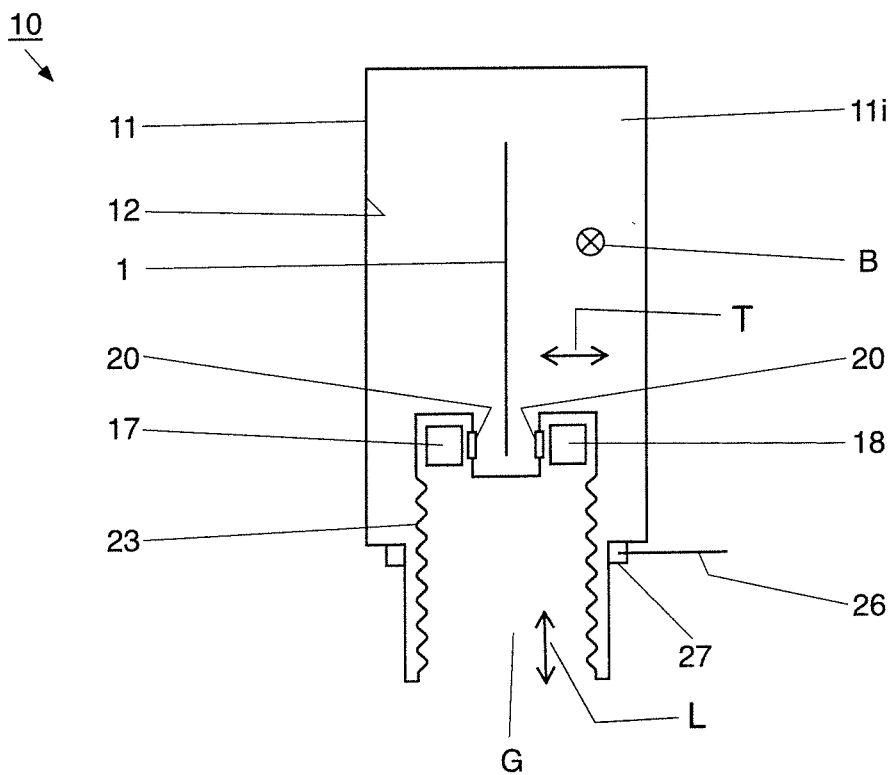

The embodiment in accordance with FIG. 24 represents a variant of the embodiment of FIG. 19, with the modification that, in this case, the first and second openings are formed in the wall 12 of the housing 11 in such a manner that they are combined to form a common opening G. Analogously to FIG. 23, with the embodiment of FIG. 24, there are expediently provided only one bellows 23, which is attached to the edges of the common opening G, and also only one adjusting device, to which the transmitting unit 17 and receiving unit 18 are each operatively connected and can be moved into the interior space 11i of the housing 11 in the longitudinal direction L when this adjusting device is actuated In the same manner as FIG. 19, the illustration of FIG. 24 also shows a cross-section through the housing 11 and the components 17, 18 in a respective operating position, when they are arranged on respective opposite sides of the strip-shaped metal product 1. Furthermore, FIG. 24 illustrates that two windows 20 are integrated in lateral regions of the bellows 23, which, in the same manner as in FIG. 19, are assigned to the transmitting unit 17 and the receiving unit.

This makes it possible to determine at least one property of the strip-shaped metal product 1 according to the transmission or penetration principle.

The embodiments in accordance with FIG. 23 and FIG. 24 are equipped in the same manner as, for example, the embodiment of FIG. 19 with closing devices 26, which is in each case attached to the housing 11 in the region of the common opening G. If the transmitting unit 17 and the receiving unit 18 are located outside the housing 11, the interior space 11*i* of the housing can be closed by means of such closing device 26, as already described above, for example, with respect to FIG. 19 or FIG. 6.

Figure 25:
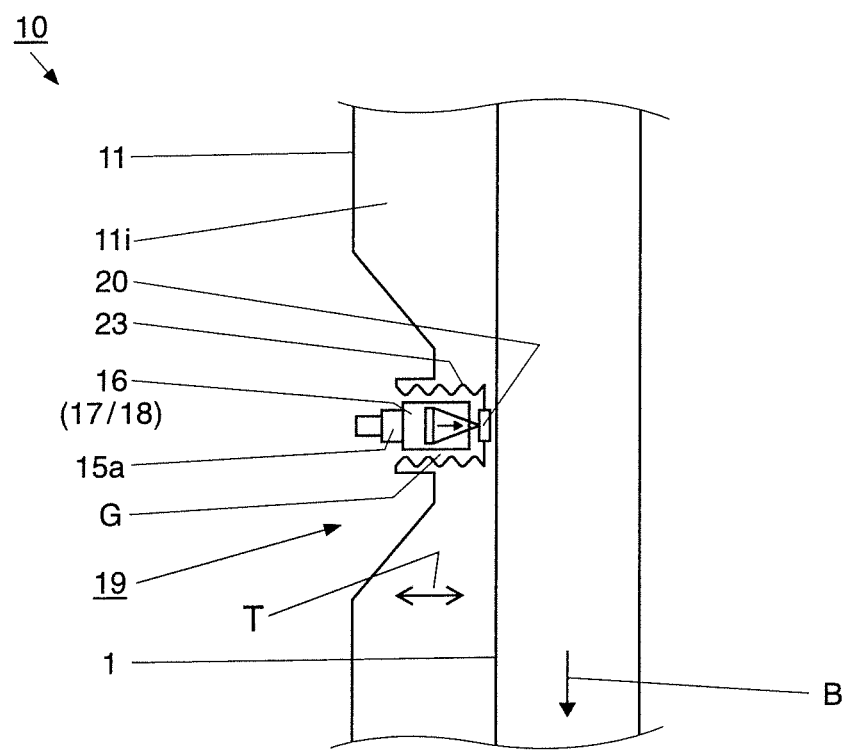
FIG. 25 shows a longitudinal sectional view through a housing of a device in accordance with a still further embodiment.

Finally, FIG. 25 shows an additional embodiment of the device 10, specifically here in a longitudinal sectional view through the housing 11 of such device 10. With regard to this embodiment, it should be emphasized that, here, the transmitting unit 17 and the receiving unit 18 of the measuring device 16 are combined to form an integrated measuring head.

With the embodiment in accordance with FIG. 25, the specified integration of the transmitting unit 17 and receiving unit 18 in a common measuring head results in such components of the measuring device 16 being arranged on the same side of the strip-shaped material 1. Accordingly, the determination of at least one property of the strip-shaped metal product is carried out here according to the reflection principle.

The embodiment in accordance with FIG. 25 is particularly suitable for the use of laser radiation generated by the transmitting unit 17 and directed onto the surface of the metal product 1, wherein the reflected part of this laser radiation is then received by the receiving unit 18. The same applies to the embodiments in accordance with FIG. 22 and FIG. 23.

With reference to the embodiment of FIG. 25, it is additionally pointed out that the measuring head shown here can alternatively also be an IMPOC measuring head. Details of the IMPOC measuring method have already been described above.

For the embodiments according to FIGS. 20-25, it may be additionally pointed out that a holding device (not shown) can also be provided here, to which the transmitting unit 17 and the receiving unit 18 are attached, analogous to the embodiment of FIG. 15 or of FIG. 19. With such a holding device, it is possible to remove or move the transmitting unit 17 and the receiving unit 18 away from the housing 11, as the case may be, after such components 17, 18 of the measuring device 16 have been moved out of the interior space 11*i* and are accordingly outside the housing 11. With regard to the implementation of possible calibration measurements, reference may be made to the descriptions on FIG. 15 in order to avoid repetitions.

With respect to all of the embodiments specified above of the device 10, it is understood that the cooling measures and/or the purge gas device shown and described in connection with FIG. 7 and FIG. 8 may also be used in this connection. It goes without saying that this involves, for example, adapting the walls 12 of the housing and/or the bellows 23 and/or the windows 20, which can each be integrated into the bellows 23, and requires no further description.

In the same manner, it is understood that, in all of the embodiments specified above of the device 10, the adjusting devices 15*a*, 15*b* used here, with which a movement for the components 17, 18 of the measuring device 16 is realized, can each be designed telescopically, as has been described, for example, for FIG. 5.

With respect to all of the embodiments specified above of the device 10, it is pointed out that, in this case, the transmitting unit 17 can be designed in such a manner that it is used to generate a laser radiation S, which is directed onto the metal product 1 and generates ultrasound in its material. Such a local ultrasonic field in the material of the metal product 1 can also be detected by means of laser radiation. This means that, for this purpose, the receiving unit 18 is then also designed to generate laser radiation, which is directed onto the metal product for the purpose of measuring the ultrasound generated in the material of the metal product 1.

The embodiments specified above of a device 10 in accordance with the present invention and a method carried out therewith in accordance with the present invention may have the following further features:

The wall 12 of the housing 11 can be formed to be double-walled at least in partial regions or everywhere. This improves the insulation of the interior space 11*i* of the housing 11 from the surrounding area without reducing the risk of a possible leakage or the escape, as the case may be, of gases out of the interior space 11*i*. Similarly, this can be improved to prevent air from the surrounding area from entering the interior space 11*i* of the housing.

A signaling device is provided for detecting damage to the strip-shaped metal product 1, for example a break ("strip break"), during its transport through the housing 11. For this case, the transmitting unit 17 and the receiving unit 18, possibly in conjunction with the respective associated bellows 23, are immediately moved out of the interior space 11*i* of the housing 11 in order to prevent damage to such components 17, 18 of the measuring device 16. After the transmitting unit 17 and the receiving unit 18 are outside the housing 1, the interior space 11*i* with its openings 13, 14, G can then be closed by means of the closing device 26.

A signaling device is provided with which a possible "flapping" of the metal product 1, i.e., an impermissible movement to the side, can be detected during its transport through the housing 11. For this case, the signal device can trigger an actuation of the movable guide rollers 28*z* in accordance with FIG. 14, which are then adjusted against the strip-shaped metal product 1 as described in FIG. 14, in order to achieve a precisely defined guidance of the metal product 1 past the transmitting unit 17 and the receiving unit 18 at least in the region of the windows 13, 14 of the housing 11 and the components 17, 18 of the measuring device 16 movably guided adjacent thereto.

A calibration measurement for the components 17, 18 of the measuring device can also be achieved by fastening a sample body (not shown) between two different batches of a metal product 1 and then transporting it through the housing 11 in the same manner as the production batches of a metal product. For example, such a sample body can be welded to the ends of a preceding metal product and a metal product used later, such that the online measurement operation does not experience any significant delay. In any case, such a sample body is then moved past the transmitting unit 17 and the receiving unit 18 in the same manner as the normal metal product 1 during transport through the housing 11, which then makes such a calibration measurement possible.

A detection device for the strip course of the metal product 1 is provided, in particular in a manner adjacent to the openings 13, 14, G of the housing 11 and the components 17, 18 of the measuring device 16 movably guided therein. At the same time, the adjusting devices 15a, 15b are each high-speed actuating cylinders that allow the transmitting unit 17 and/or the receiving unit to be moved at a high response or adjustment speed, as the case may be. In the same manner, the adjusting means for the bellows 23 can also be designed in such a manner that they can be used to move the bellows 23 connected thereto in a very short time or at a high response speed, as the case may be. The specified detection device is connected in terms of signal technology to the adjusting devices or high-speed actuating cylinders, as the case may be, and also to the adjusting means for the bellows. As a result, it is possible for the transmitting unit 17 and/or receiving unit 18 to be moved away from the metal product 1 very quickly, if the latter undergoes an unscheduled movement towards the side, i.e., in the direction of the components 17, 18 of the measuring device 16. As a result, damage to such components 17, 18 can be prevented. Expediently, the respective bellows 23 are then moved away from the metal product synchronously or simultaneously, as the case may be, with their associated components 17, 18 of the measuring device 16. For such an embodiment of the invention, it is possible to set the distance between, on the one hand, the transmitting unit 17 and/or the receiving unit 18 and, on the other hand, the metal product as well to values<10 mm.

LIST OF REFERENCE SIGNS

1 Metal product
10 Device
11 Housing
11i Interior space (of the housing 11)
12 Wall
13 First opening
14 Second opening
15a Adjusting device
15b Adjusting device
16 Measuring device
17 Transmitting unit (as a component of the measuring device 16)
18 Receiving unit (as a component of the measuring device 16)
19 Narrow point (of the housing 11)
20 Shield (e.g., in the form of a window)
21 Individual layers or plies, as the case may be (of a shield or window 20, as the case may be)
22 Cavity
23 Deformable sealing device (e.g., in the form of a bellows)
24 Cooling device
25 Line coil or cooling channel
26 Closing device
27 Container (for sealing device 26)
28 Protective sliding device (e.g., in the form of a rotatably mounted guide roller)
30 Cooling line or cavity
32 Adjusting means (for the deformable sealing device 23)
33 Support structure (for the deformable sealing device 23)
B Direction of movement (for metal product 1)
F Direction in which purge gas is directed onto the window 20
G Common opening (in the wall 12 of the housing 11)
H Holding device
K Cooling fluid
L Longitudinal movement (of a component 17, 18 of the measuring device 16)
S Signal emitted by the transmitting unit 17
S' Signal received by the receiving unit 18
T Transverse movement (of a component 17, 18 of the measuring device 16)
U Surrounding area (of the housing 11)

The invention claimed is:

1. A device (10) for contactless determination of at least one property of a metal product (1) during metallurgical production of the metal product (1), comprising:
   a housing (11) through which the metal product (1) is movable;
   a first opening (13) and a second opening (14) formed in a wall (12) of the housing (11),
   at least one measuring device (16) comprising
      a transmitting unit (17) and
      a receiving unit (18),
      wherein an electromagnetic field is generated by the transmitting unit (17) and directed onto the metal product (1) and thereby a physical interaction is induced in a material of the metal product (1), and
      wherein a remaining and/or resulting part of this physical interaction is received by the receiving unit (18); and
   wherein the transmitting unit (17) is associated with the first opening (13), such that the electromagnetic field generated by the transmitting unit (17) impinges on the metal product (1) on a side of the first opening (13),
   wherein the receiving unit (18) is associated with the second opening (14), such that the remaining and/or resulting part of the physical interaction induced in the material of the metal product (1) is received by the receiving unit (18) on a side of the second opening (14), and
   wherein at least one adjusting device (15a, 15b) is provided outside the housing (11), by which at least one of the transmitting unit (17) and the receiving unit (18) can be moved relative to the wall (12) of the housing (11) in a region of the first opening (13) or the second opening (14) or adjacent thereto, in order to thereby set or selectively change a predetermined distance between the at least one of the transmitting unit (17) and the receiving unit (18) and the metal product (1).

2. The device (10) according to claim 1,
   wherein the metal product (1) is a strip-shaped material,
   wherein the at least one adjusting device (15a, 15b) is arranged in such a manner that, thereby, the transmitting unit (17) and/or the receiving unit (18) are each movably adjustable in a transverse direction (T) orthogonal to a surface of the strip-shaped material (1) and/or in a longitudinal direction (L) parallel to a surface of the strip-shaped material (1).

3. The device (10) according to claim 1,
   wherein the metal product (1) is a strip-shaped material,
   wherein a holding device (H) is provided outside the housing (11), to which the transmitting unit (17) and/or the receiving unit (18) is/are attached, and
   wherein the holding device (H) is movably adjustable with respect to the metal product (1) in a longitudinal direction (L) parallel to a surface of the strip-shaped material (1).

4. The device (10) according to claim 1,
wherein the housing (11) has a narrow point (19) in a region of the first opening (13) and/or the second opening (14).

5. The device (10) according to claim 1,
wherein the housing (11) is part of a furnace for heat treatment and/or part of a plant for coating the metal product (1).

6. The device (10) according to claim 1,
wherein, in the region of the first opening (13) and of the second opening (14), there is provided in each case a shield (20) in form of a window which is transparent with respect to the electromagnetic field or an associated physical effect.

7. The device according to claim 6,
wherein the shield (20) is designed to reduce heat radiation through the first opening (13) and the second opening (14) from an interior space (11i) of the housing (11) to a surrounding area (U).

8. The device (10) according to claim 6,
wherein the shields (20) are respectively fastened inside the first opening (13) and the second opening (14), thereby closing an interior space (11i) of the housing (11) with respect to a surrounding area (U).

9. The device (10) according to claim 6,
wherein the shield (20) is connected to an elastically deformable sealing device (23) in the form of a deformable bellows, and
wherein the sealing device (23) is fastened to edges of the first and second openings (13, 14), respectively, and thereby seals an interior space (11i) of the housing (11) with respect to a surrounding area (U).

10. The device (10) according to claim 9,
wherein at least a frontal and/or lateral section of the sealing device (23) is equipped with a protective layer against electromagnetic and/or thermal radiation.

11. The device according to claim 9,
further comprising a telescopic adjusting means (32) to which the sealing device (23) is operatively connected,
wherein, upon actuation of the telescopic adjusting means (32) the shield (20) connected to the sealing device (23) is movable into or out of the housing (11).

12. The device according to claim 9,
further comprising support means (33) for the sealing device (23) along its longitudinal extension, which support means (33) stabilizes the sealing device (23) in its longitudinal direction.

13. The device (10) according to claim 1,
wherein the at least one adjusting device (15a, 15b) is designed in such a manner that the transmitting unit (17) or the receiving unit (18) connected thereto is movable into the housing (11), and
wherein the at least one adjusting device (15a, 15b) is formed to be telescopic.

14. The device (10) according to claim 9, further comprising
at least one cooling device (24) and/or
at least one purge gas device (F),
by which the shields or windows (20) and/or the transmitting unit (17) and the receiving unit (18) and/or the sealing device (23) can be cooled and/or can be acted upon by a purge gas.

15. The device (10) according to claim 9, further comprising
a cooling device (24) with at least one cooling line (30) or cavity that is formed in the wall (12) of the housing (11) or in a material of the sealing device (23),
wherein the cooling device (24) comprises a line coil (25) that is attached to the transmitting unit (17) or the receiving unit (18); and
a purge gas device (F) attached adjacent to a shield (20), the transmitting unit (17), or the receiving unit (18).

16. The device (10) according to claim 15,
wherein the shields or windows (20) are formed in multiple layers and
wherein a cavity (K) is formed between individual ones of the multiple layers (21), and
wherein the cavity (K) is flowed through with cooling gas.

17. The device (10) according to claim 1,
wherein the first opening (13) and the second opening (14) are respectively formed in opposite sides of the wall (12) of the housing (11) and
wherein, correspondingly, the transmitting unit (17) and the receiving unit (18) are arranged on opposite sides of the metal product (1).

18. The device (10) according to claim 1,
wherein the first opening (13) and the second opening (14) are each formed on the same side of the wall (12) of the housing (11) and
wherein, correspondingly, the transmitting unit (17) and the receiving unit (18) are arranged on a same side of the metal product (1).

19. The device according to claim 18,
wherein the first opening (13) and the second opening (14) are formed as a common opening (G) in the wall (12) of the housing (11).

20. The device (10) according to claim 1,
further comprising a closing device (26) in each case in the region of the first opening (13) and/or of the second opening (14),
wherein the first opening (13) and/or the second opening (14) is closable by the closing device (26) if the associated transmitting unit (17) or the receiving unit (18) is located outside the housing (11) and thus outside the first or second opening (14).

21. The device (10) according to claim 9, further comprising
protective sliding devices (28) in an interior space (11i) of the housing (11), with which a spacing of the metal product (1) guided in the interior space (11i) of the housing (11) from the first opening (13) and/or the second opening (14) and/or from the transmitting unit (17) and the receiving unit (18) and/or from the sealing device (23) is ensured,
wherein the protective sliding devices (28) are rotatably mounted guide rollers.

22. The device (10) according to claim 21,
wherein the rotatably mounted guide rollers (28z) are
translationally movable within the housing (11), in order to thereby come into contact with the metal product (1) or to exert a compressive force on the metal product (1), and
arranged in a manner adjacent to the first opening (13) or the second opening (14) on one side of the metal product (1),
wherein a spacing of such rotatably mounted guide rollers (28z) from one another is different from a spacing that two further protective sliding devices (28) arranged on an opposite side of the metal product (1) have.

23. The device (10) according to claim 1,
wherein the transmitting unit (17) emits X-ray radiation, and wherein the receiving unit (18) is designed to receive any remaining and/or resulting X-ray radiation (S') based on the physical interaction with the material of the metal product (1).

24. The device (10) according to claim 1,
wherein the transmitting unit (17) emits laser beams (S), and
wherein the receiving unit (18) is designed to receive or detect the physical interaction induced in the material of the metal product (1) by the laser beams generated by the transmitting unit (17).

25. The device (10) according to claim 1,
wherein the transmitting unit (17) and the receiving unit (18) are components of an IMPOC measuring head,
wherein the transmitting unit (17) is a magnetizing coil and the receiving unit (18) is a magnetic field sensor.

26. A method for contactless determination of at least one property of a metal product (1) during metallurgical production of the metal product (1), comprising:
moving the metal product (1) through a housing (11),
providing a measuring device (16) comprising
a transmitting unit (17) and
a receiving unit (18);
generating an electromagnetic field by the transmitting unit and directing the electromagnetic field onto the metal product (1), thereby
inducing a physical interaction in a material of the metal product (1);
subsequently receiving a remaining and/or resulting part of this physical interaction by the receiving unit (18);
moving the transmitting unit (17) and/or the receiving unit (18) relative to the housing (11) or the metal product (1) in a region of an opening (13, 14) of the housing (11) or adjacent thereto;
thereby setting or selectively changing a predetermined distance between the metal product (1) and the transmitting unit (17) and/or the receiving unit (18).

27. The method according to claim 26,
wherein the transmitting unit (17) and/or the receiving unit (18) are moved into or out of the housing (11) by an adjusting device (15a, 15b).

28. The method according to claim 26,
wherein the metal product (1) is a strip-shaped material, and
wherein the moving of the transmitting unit (17) and/or the receiving unit (18) is performed in a transverse direction (T) orthogonal to a surface of the strip-shaped material (1).

29. The method according to claim 28,
wherein, by moving the transmitting unit (17) and/or the receiving unit (18) in the transverse direction (T), a changed position of the metal product (1) within the housing (11) and/or a changed distance between the transmitting unit (17) and/or the receiving unit (18) and the metal product (1) is compensated.

30. The method according to claim 26,
wherein the metal product (1) is a strip-shaped material and
wherein a holding device (H) is provided, to which the transmitting unit (17) and the receiving unit (18) are attached,
wherein moving the transmitting unit (17) and the receiving unit (18) is performed by adjusting the holding device (H) with respect to the metal product (1) in a longitudinal direction (L) parallel to a surface of the strip-shaped material (1).

31. The method according to claim 26,
wherein the metal product (1) is a strip-shaped material,
wherein moving the transmitting unit (17) and/or the receiving unit (18) in a longitudinal direction (L) parallel to a surface of the strip-shaped material (1) is performed.

32. The method according to claim 26,
wherein the metal product (1) is a strip-shaped material and
wherein a holding device (H) is provided, to which the transmitting unit (17) and the receiving unit (18) are attached,
wherein moving the transmitting unit (17) and the receiving unit (18) is performed by adjusting the holding device (H) with respect to the metal product (1) in a transverse direction (T) orthogonal to a surface of the strip-shaped material (1).

33. The method according to claim 30,
wherein, by moving the holding device (H), the transmitting unit (17) and/or the receiving unit (18) are removed from the housing (11), and
wherein subsequently calibration and/or maintenance work of the transmitting unit (17) and/or the receiving unit (18) is performed.

34. The method according to claim 26,
wherein openings (13, 14) are formed in a wall (12) of the housing (11) adjacent to the transmitting unit (17) and the receiving unit (18) respectively, and
wherein, in a region of the openings (13, 14), the transmitting unit (17) or receiving unit (18) and/or shields (20) in form of windows, which are provided in the region of the openings (13, 14) and which are transparent with respect to radiation waves of the electromagnetic field or its field lines, are locally cooled and/or acted upon by purge gas (F).

35. The method according to claim 26,
wherein electromagnetic radiation (S) in form of X-ray radiation or laser radiation is emitted with associated waves by the electromagnetic field generated by the transmitting unit (17).

36. The method according to claim 26,
wherein the material of the metal product (1) is magnetized by the electromagnetic field generated by the transmitting unit (17),
wherein the receiving unit (18) is designed as a magnetic field sensor to measure a gradient of a residual magnetic field strength ($A/m^2$).

37. The method according to claim 26,
wherein the metal product (1) is heat-treated and/or coated during its transport through the housing (11).

38. The method according to claim 26,
wherein the property of the metal product (1) is at least one quantity selected from the group consisting of microstructure, phase fraction, degree of recrystallization, grain size, texture, pole figure, orientation distribution function, oxidation layer and a mechanical characteristic value.

* * * * *